(12) United States Patent
Penny et al.

(10) Patent No.: US 12,274,518 B2
(45) Date of Patent: Apr. 15, 2025

(54) ELECTROMECHANICAL SURGICAL SYSTEM

(71) Applicant: Asensus Surgical US, Inc., Durham, NC (US)

(72) Inventors: Matthew Robert Penny, Holly Springs, NC (US); James A Woodard, Raleigh, NC (US)

(73) Assignee: Asensus Surgical US, Inc., Durham, NC (US)

( * ) Notice: Subject to any disclaimer, the term of this patent is extended or adjusted under 35 U.S.C. 154(b) by 1136 days.

(21) Appl. No.: 17/064,039

(22) Filed: Oct. 6, 2020

(65) Prior Publication Data

US 2021/0093311 A1 Apr. 1, 2021

Related U.S. Application Data

(63) Continuation of application No. 17/063,974, filed on Oct. 6, 2020, which is a continuation of application No. 16/160,960, filed on Oct. 15, 2018, now Pat. No. 11,497,481, which is a continuation of application No. PCT/US2017/027818, filed on Apr. 14, 2017.

(Continued)

(51) Int. Cl.
| A61B 34/30 | (2016.01) |
| A61B 17/00 | (2006.01) |
| A61B 34/00 | (2016.01) |
| A61B 46/10 | (2016.01) |

(52) U.S. Cl.
CPC ........ *A61B 34/30* (2016.02); *A61B 17/00234* (2013.01); *A61B 34/70* (2016.02); *A61B 34/71* (2016.02); *A61B 46/10* (2016.02); *A61B 2017/003* (2013.01); *A61B 2017/00327* (2013.01); *A61B 2017/00367* (2013.01); *A61B 2017/00398* (2013.01); *A61B 2017/00477* (2013.01); *A61B 2017/00876* (2013.01); *A61B 2034/301* (2016.02); *A61B 2034/302* (2016.02); *A61B 2034/303* (2016.02)

(58) Field of Classification Search
CPC ........ A61B 2034/303; A61B 2034/301; A61B 2017/00876; A61B 2017/00477; A61B 2017/00398; A61B 2017/00367; A61B 2017/00327; A61B 2017/00323; A61B 2017/00296; A61B 46/10
See application file for complete search history.

(56) References Cited

U.S. PATENT DOCUMENTS

2013/0110129 A1* 5/2013 Reid ............... A61B 34/30
403/326

* cited by examiner

*Primary Examiner* — Jocelin C Tanner

(57) ABSTRACT

A surgical system includes a drive unit on a support. The drive unit includes motors or other actuators and a plurality of output elements arranged such that operation of each drive unit linearly translates a corresponding one of the output elements. A surgical device has actuation elements extending through an elongate shaft to a distal articulation section, and an input subsystem carried at the proximal end of the shaft. Linear translatable input elements or pistons of the input subsystem are each associated with a corresponding one of the actuation elements. The input and output elements are positioned such that operation of an actuator linearly translates an output element, causing linear translation of a corresponding input element and engagement of an actuation element. A sterile drape is positionable between the input elements and the output elements.

14 Claims, 22 Drawing Sheets

Related U.S. Application Data

(60) Provisional application No. 62/322,529, filed on Apr. 14, 2016, provisional application No. 62/322,539, filed on Apr. 14, 2016, provisional application No. 62/322,585, filed on Apr. 14, 2016.

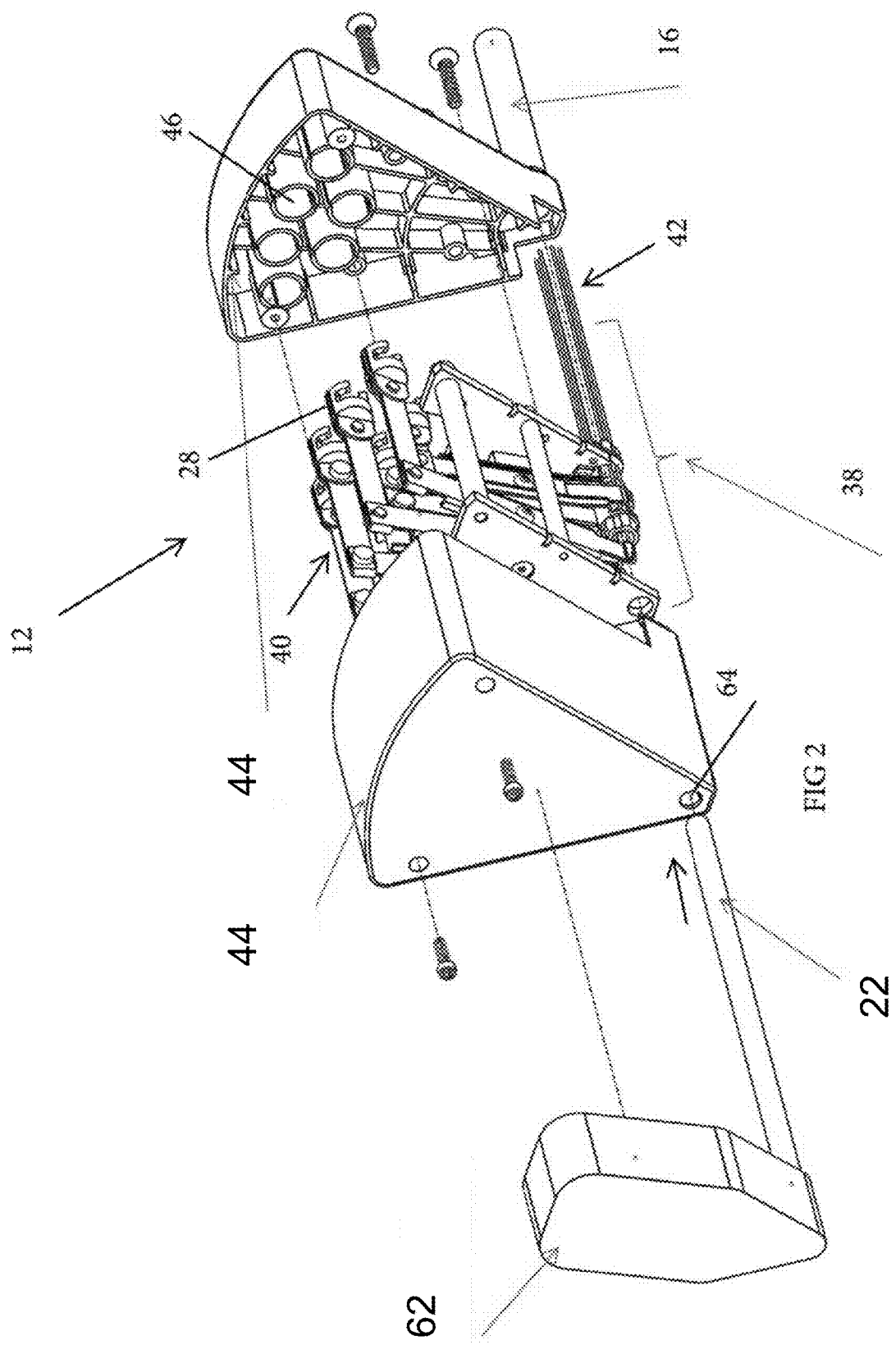

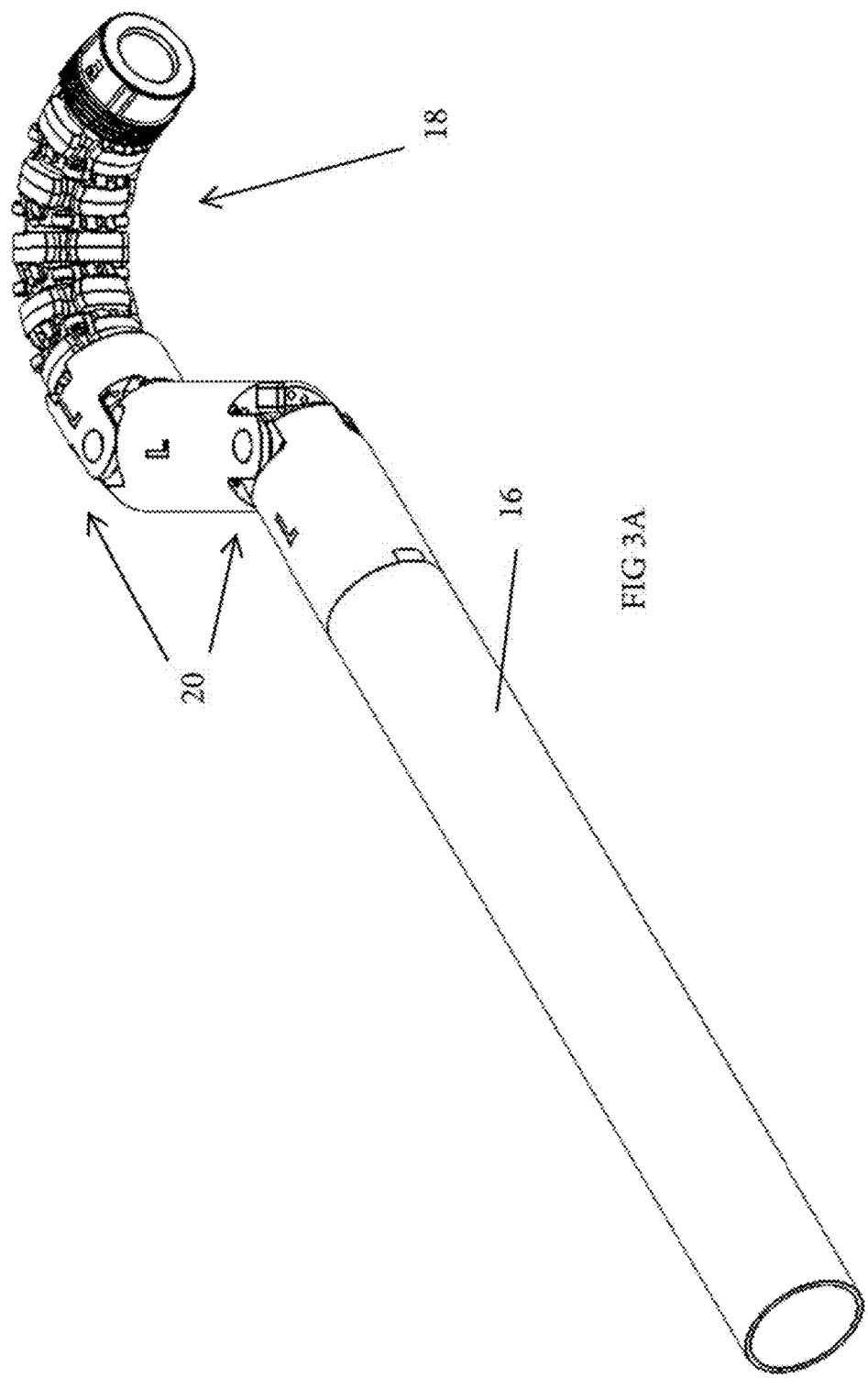

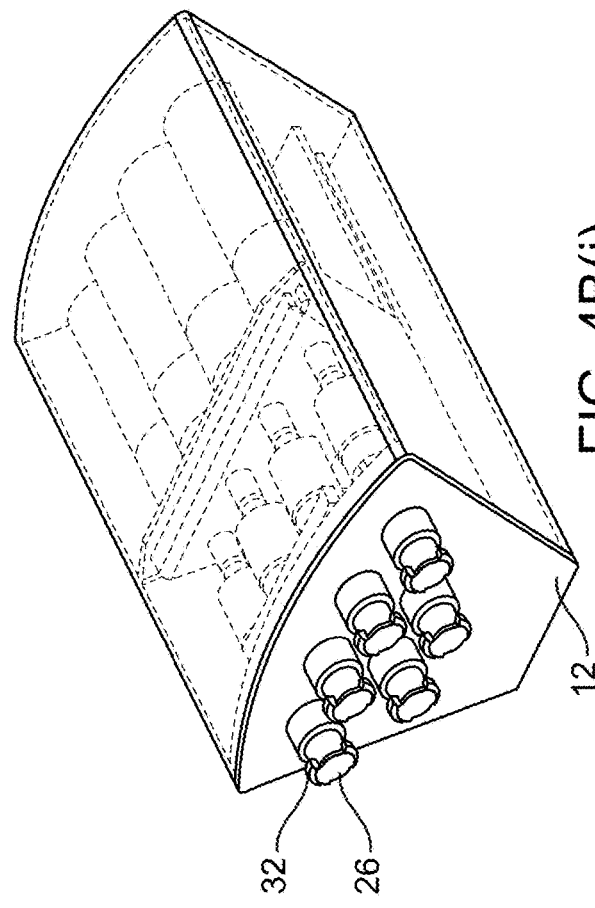
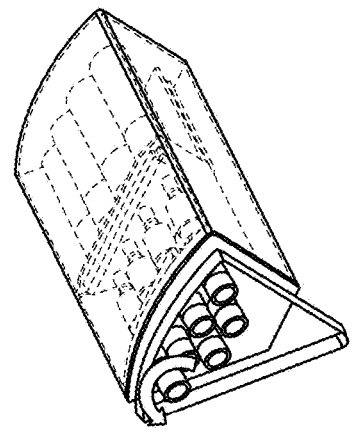
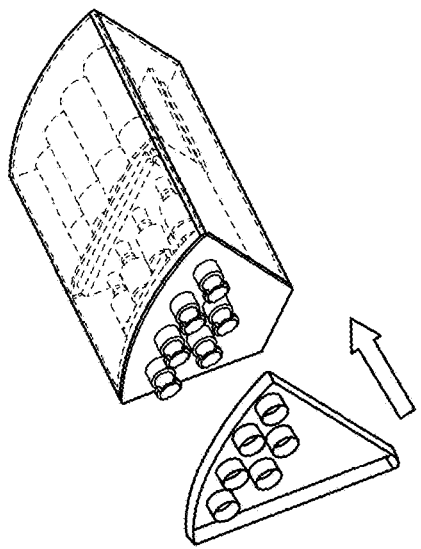
FIG. 4B(i)
FIG. 4B(ii)
FIG. 4B(iii)

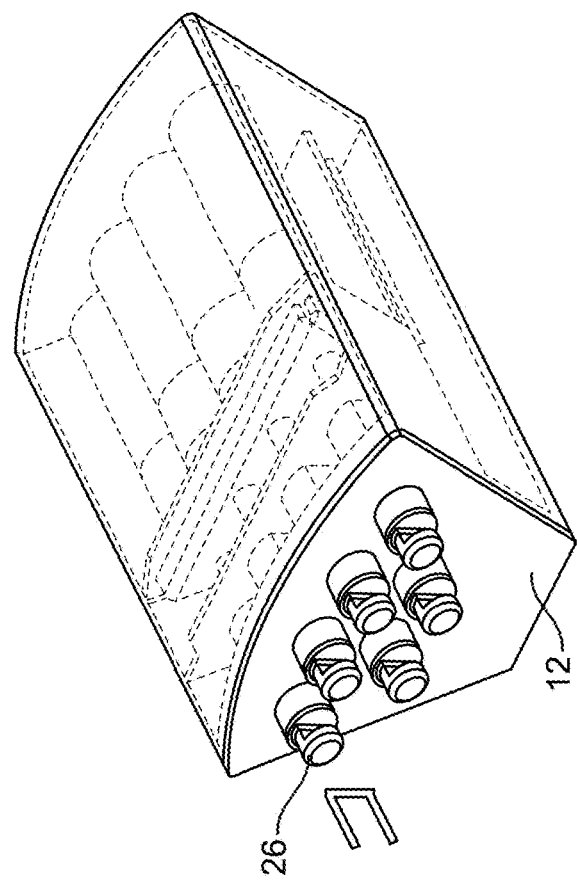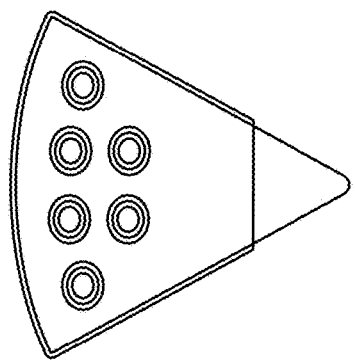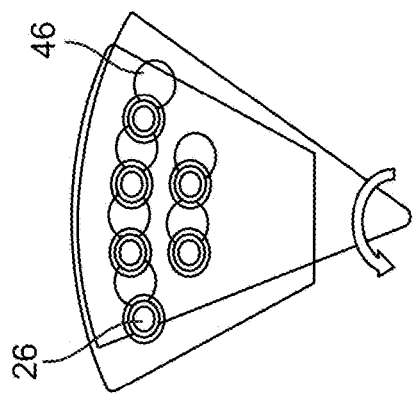

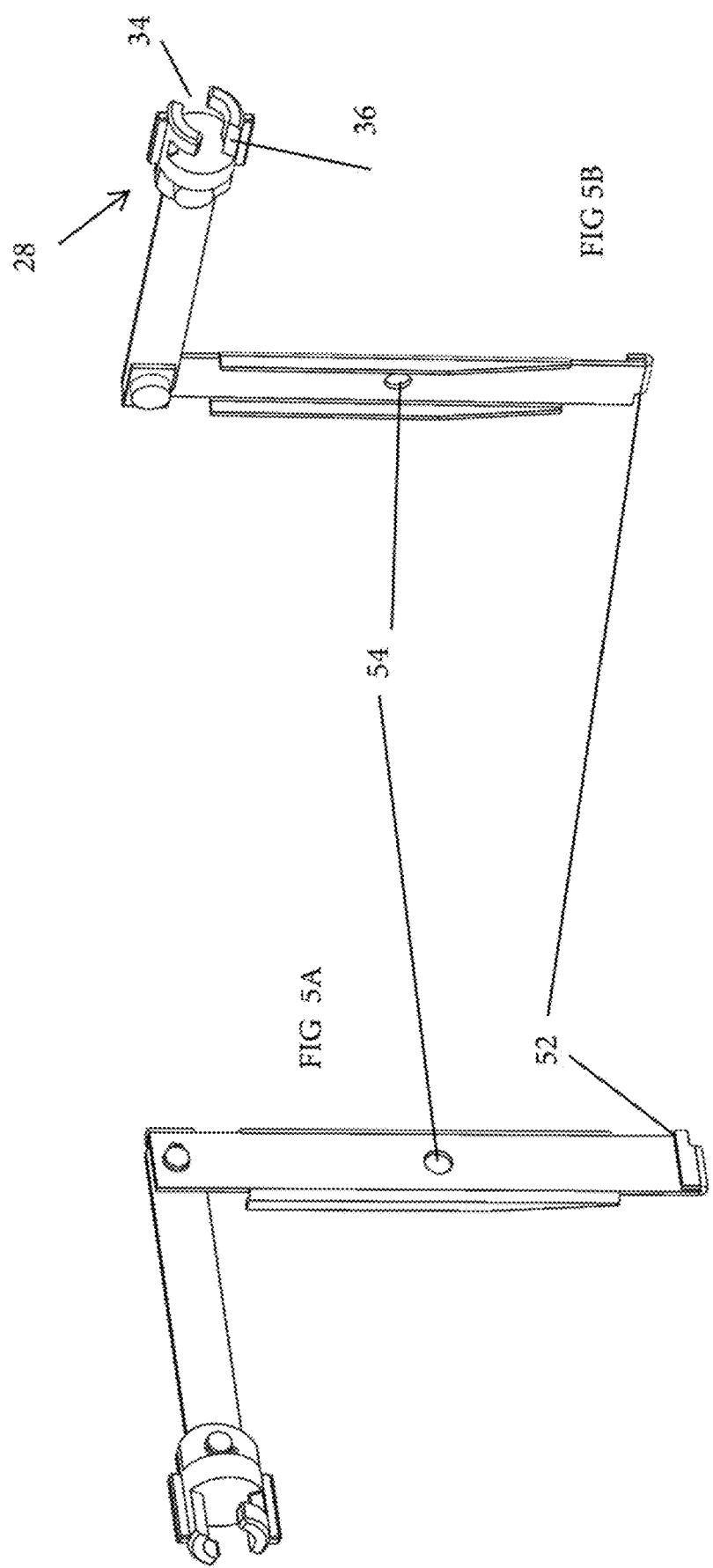

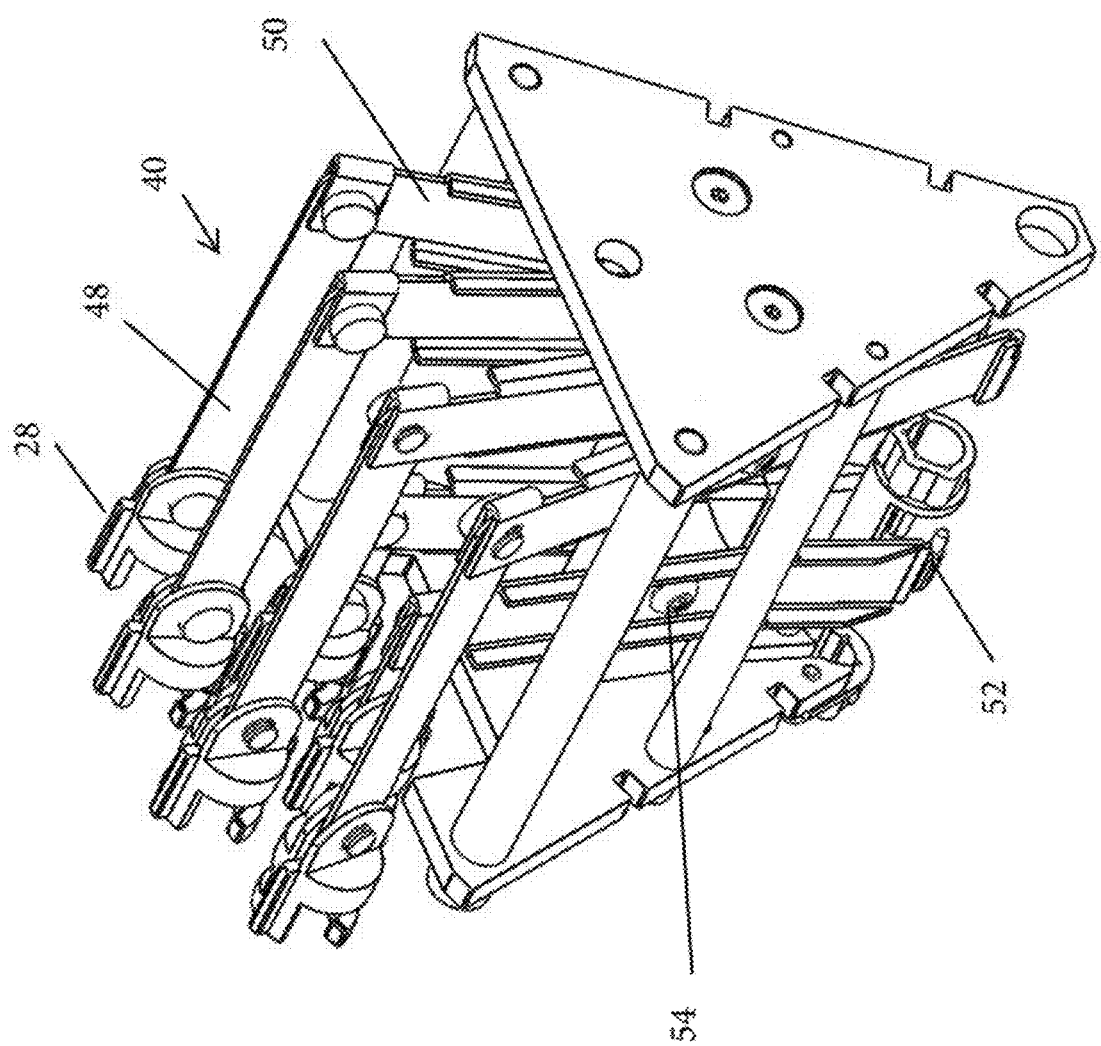

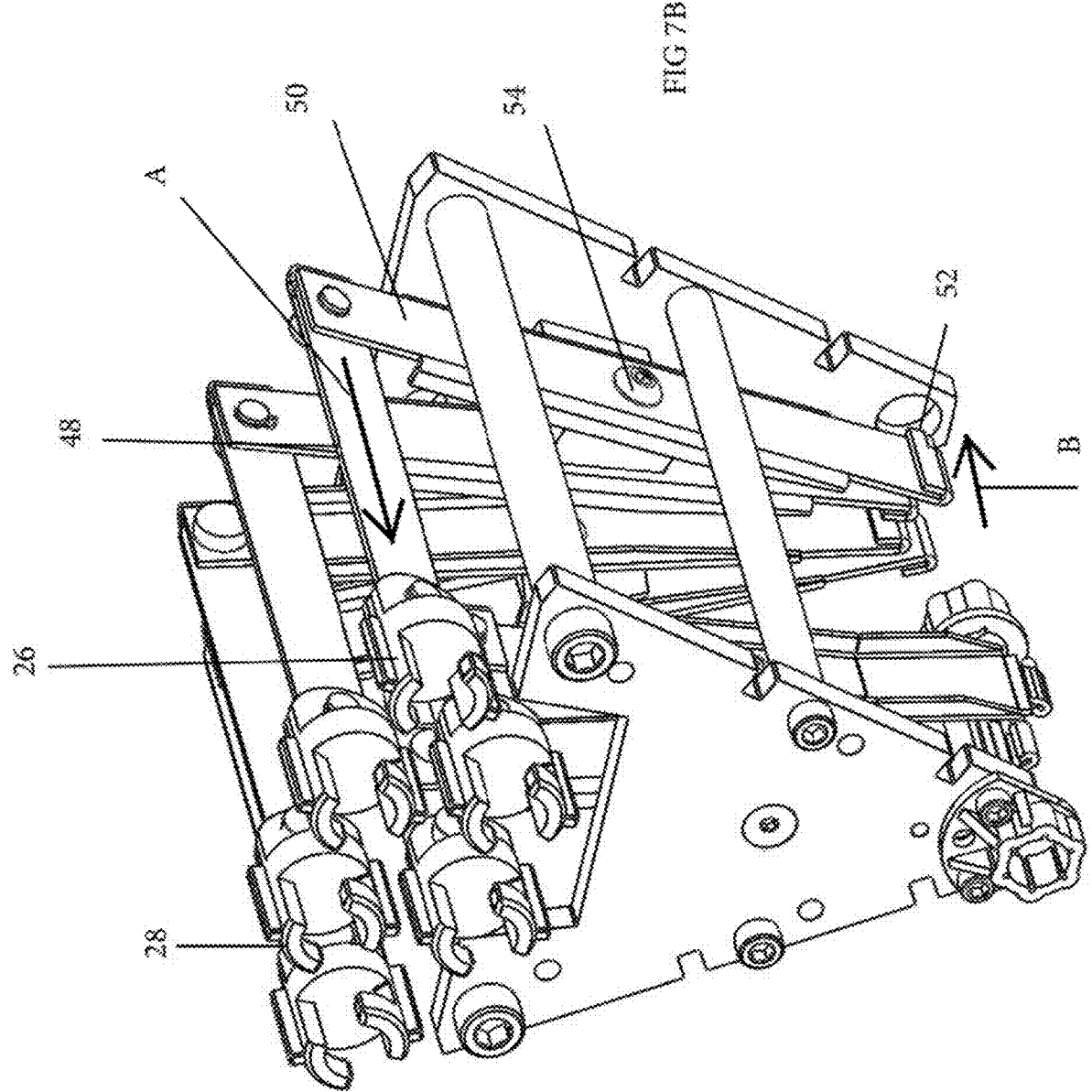

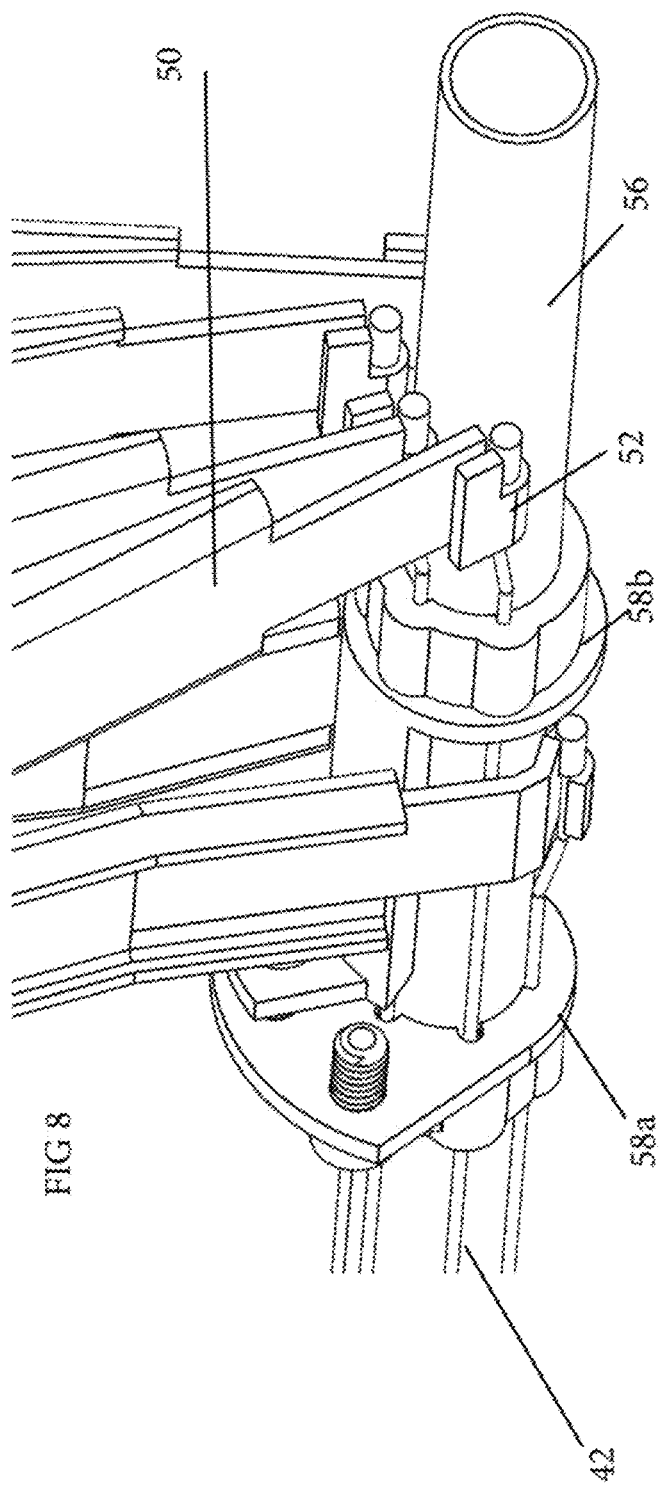

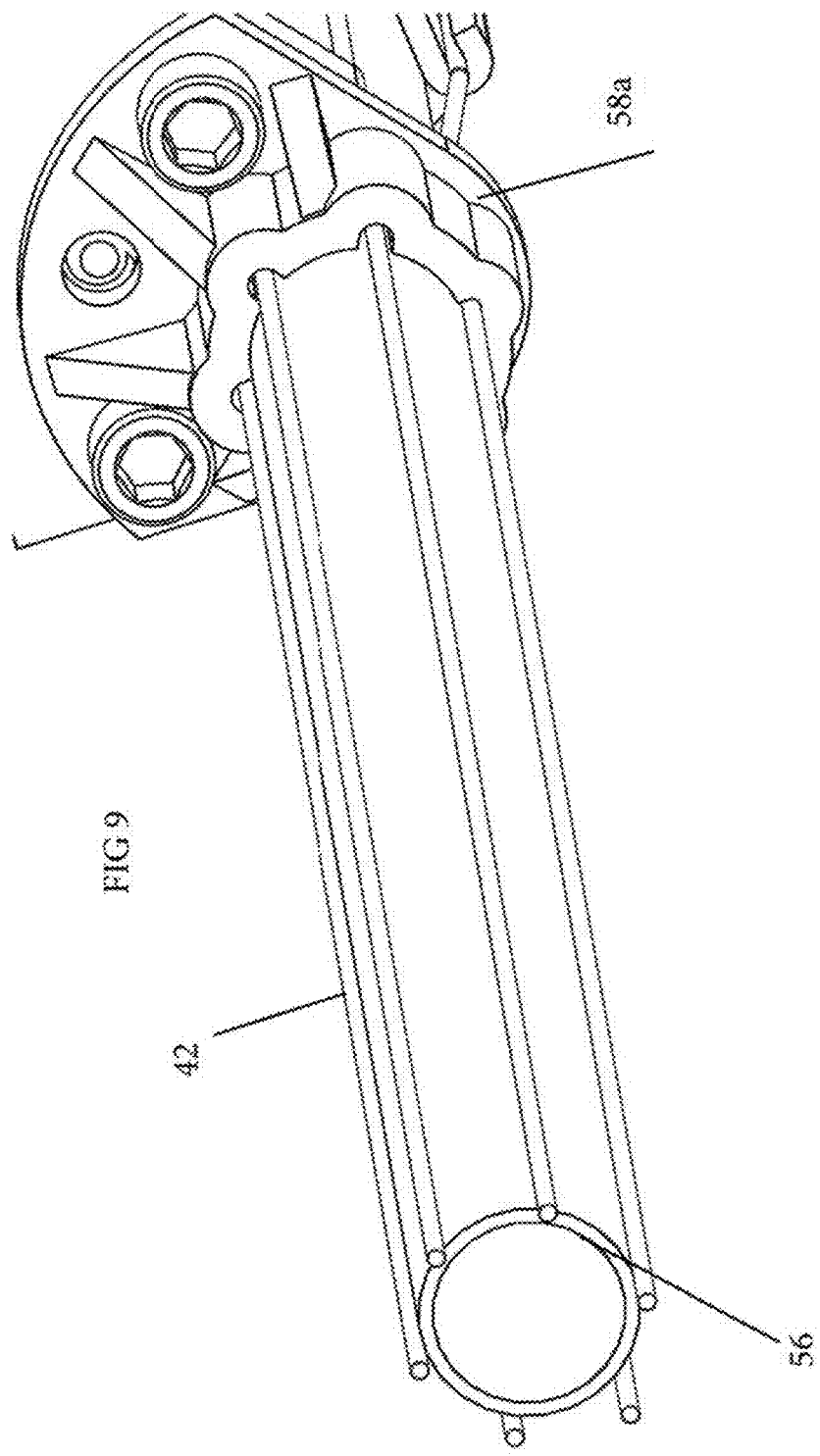

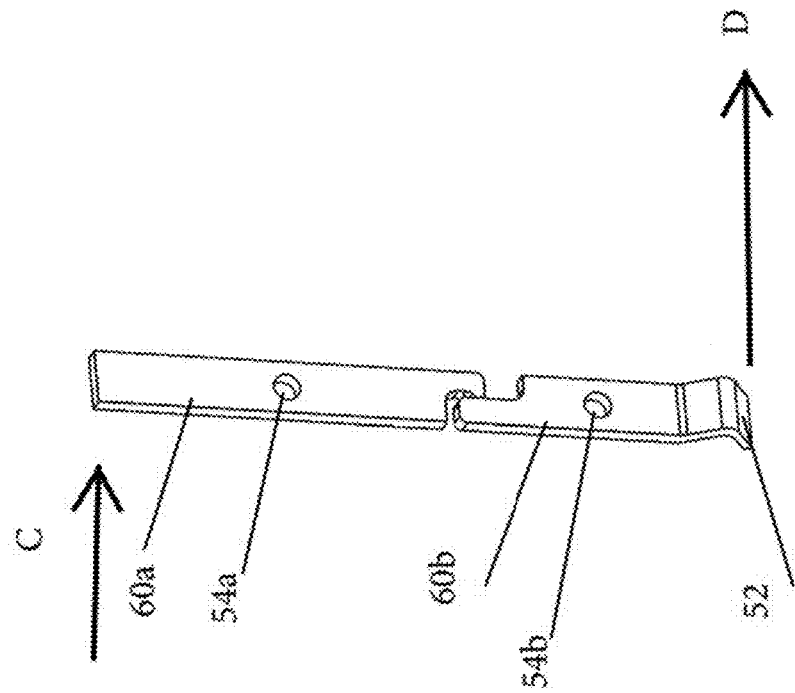
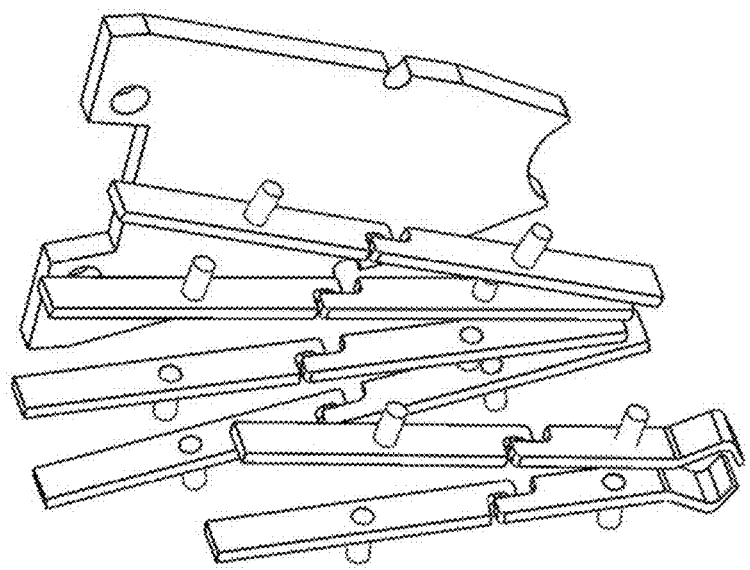

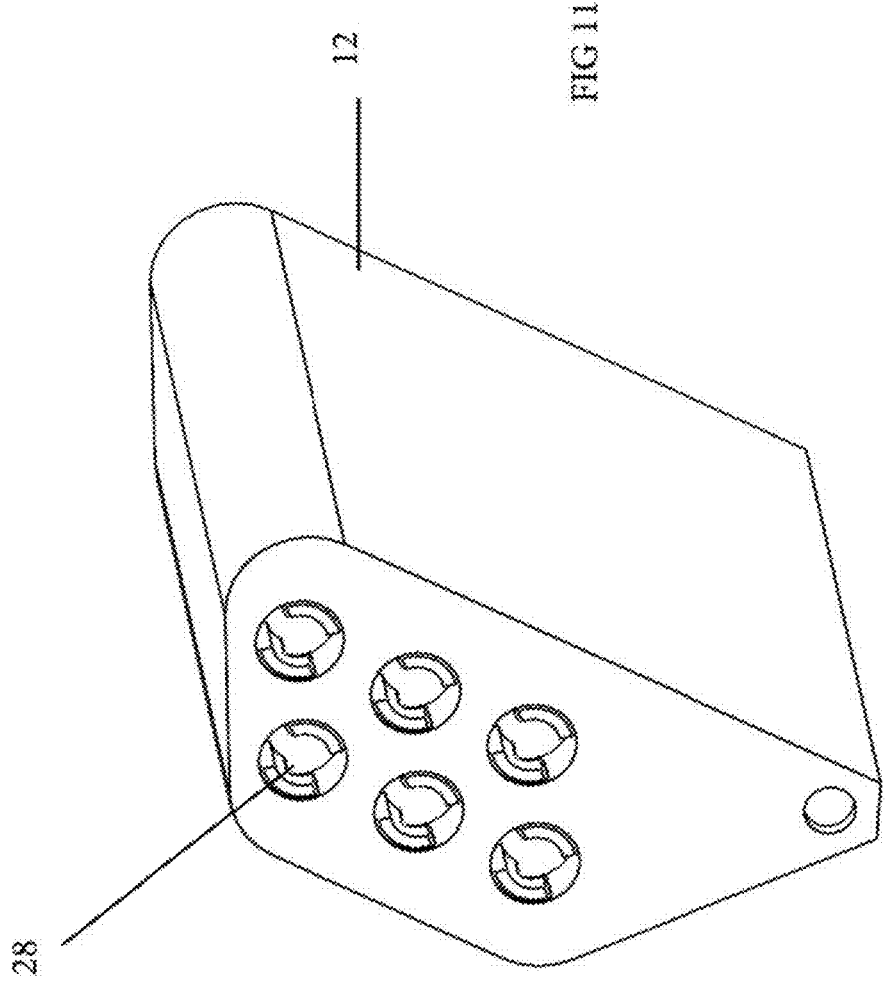

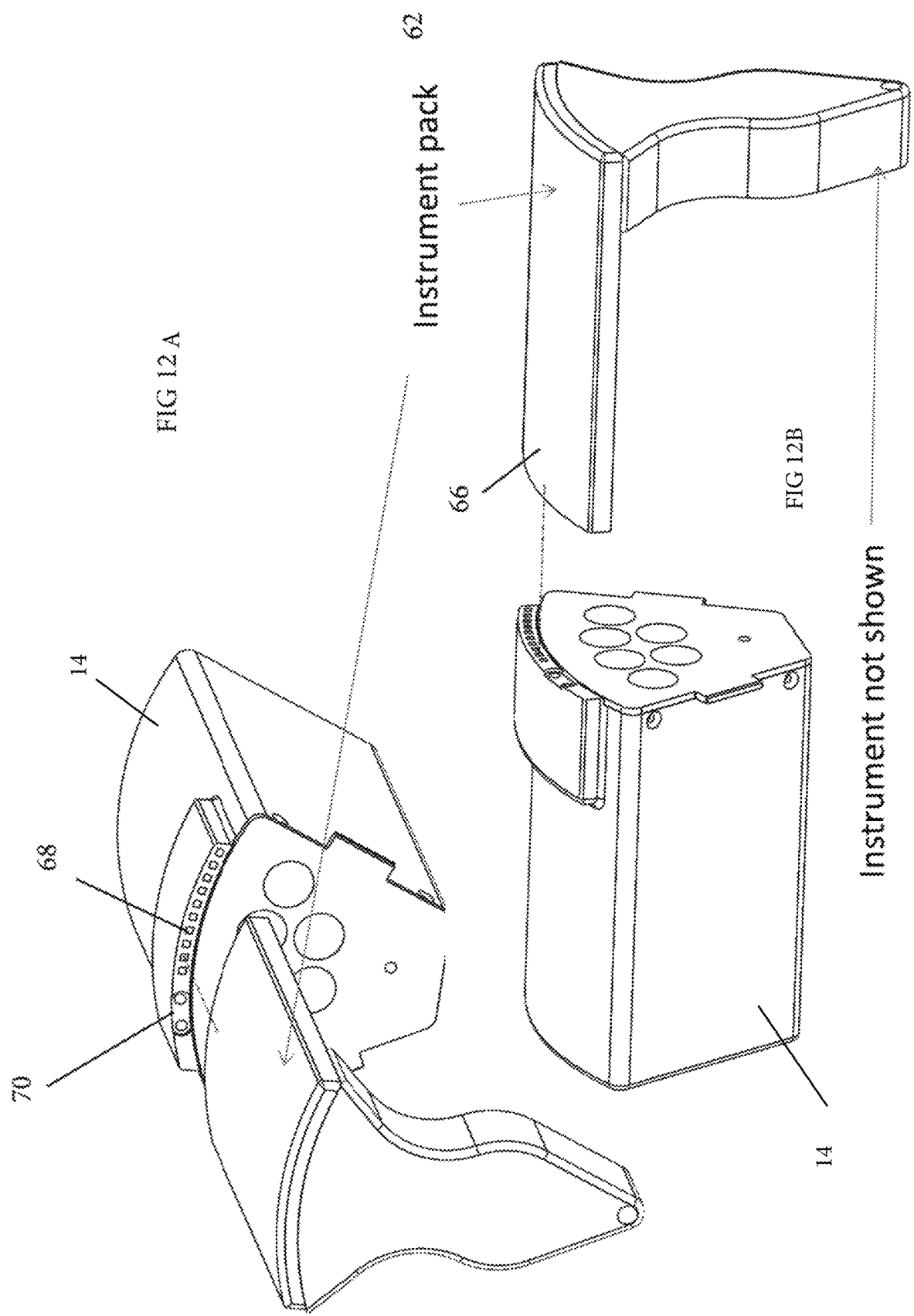

ELECTROMECHANICAL SURGICAL SYSTEM

This application is a continuation of U.S. Ser. No. 16/160,190, filed Oct. 15, 2018, which is a continuation of PCT/US2017/027818, filed Apr. 14, 2017, which claims the benefit of each of the following provisional applications: U.S. 62/322,585, filed Apr. 14, 2016, U.S. 62/322,529, filed Apr. 14, 2016, and 62/322,539, filed Apr. 14, 2016, each of which is incorporated herein by reference for all purposes.

TECHNICAL FIELD OF THE INVENTION

The present invention relates to the field of surgical systems using electromechanical drivers to effect movement of medical instruments within a body cavity.

BACKGROUND

Surgical systems used for robotically-assisted surgery or robotic surgery employ electromechanical drivers to drive movement of surgical devices within a body cavity, typically in response to signals generated when a user moves a user input device. The surgical devices may be surgical instruments having end effectors, and/or they may be steerable lumen devices adapted to receive such surgical instruments (or a combination of such surgical instruments and lumen devices). The surgical devices include actuation elements (e.g. wires, rods or cables) that, when pushed and/or pulled, cause active bending or articulation at the distal end of the surgical device, which is disposed within a patient's body. Motion produced by the electromechanical drivers is used to push and/or pull the actuation elements to produce this bending or articulation.

In such systems, it is desirable to avoid the need to sterilize components housing motors and electronics. Instead, prior art surgical systems provide the driver (which houses the motors and some electronics) as a component that may be covered with a sterile drape in the surgical procedure room. The surgical device that is to be driven by the driver is a separate, sterile, component removably mounted to the driver in a manner that allows the sterile drape to maintain a sterile barrier between the driver and the surgical device. Features are provided for transferring the mechanical output of the motors in the driver to the actuation elements in the surgical device, so that actuation of the motors causes the desired movement of the distal part of the surgical device within the patient's body cavity.

In many prior art systems, the mechanical output features of the driver take the form of rotating output elements such as shafts, disks or other elements which rotate when the motors in the driver are energized. Each such output element is rotationally coupled to a corresponding rotatable input elements on the surgical device that, when rotated, causes the pushing or pulling of the surgical device's actuation elements. To maintain the sterile boundary provided by the surgical drape that is disposed between the driver and the surgical device, the rotational motion from each rotating output element is transferred to its corresponding rotatable input element using intermediate sterile rotating pieces (e.g. rotating disks) that receive the rotational motion from the output elements of the driver and transfer the rotational motion to the input elements of the surgical device.

The present application describes an alternate system for transferring motion between an electromechanical drive and a surgical device in a surgical system.

BRIEF DESCRIPTION OF THE DRAWINGS

FIG. 2 is a perspective view of the surgical device and instrument, in which the surgical device is shown in exploded view.

FIG. 3A is a perspective view of a shaft of a lumen device.

FIG. 4B(i) is a perspective view of the motor drive of FIG. 4A, and FIGS. 4B(ii) and 4(B)(iii) schematically illustrate the manner of engaging the bayonet connection.

FIG. 4C(i) is a perspective of the motor drive having an alternative mechanism for engaging the output and input elements, and 4C(ii) and 4C(iii) schematically illustrate the manner of engaging those elements.

FIGS. 5A and 5B are perspective views of the linkage assemblies of the surgical device of FIG. 2.

FIGS. 7A and 7B are perspective views showing the linkage assemblies of the surgical device of FIG. 2.

FIG. 8 shows the cable interface of the surgical device of FIG. 2.

FIG. 9 shows the cable interface viewed in a proximal direction.

FIGS. 10A and 10B show an alternative link arm for use in a linkage assembly of the type shown in FIGS. 5A and 5B.

FIG. 11 shows an alternative housing shape for the surgical device and an alternative arrangement of input elements.

FIGS. 12A and 12B illustrates mechanical and electrical coupling between the instrument pack and the motor drive. In these figures the surgical device is not shown.

DESCRIPTION

Figure 1:
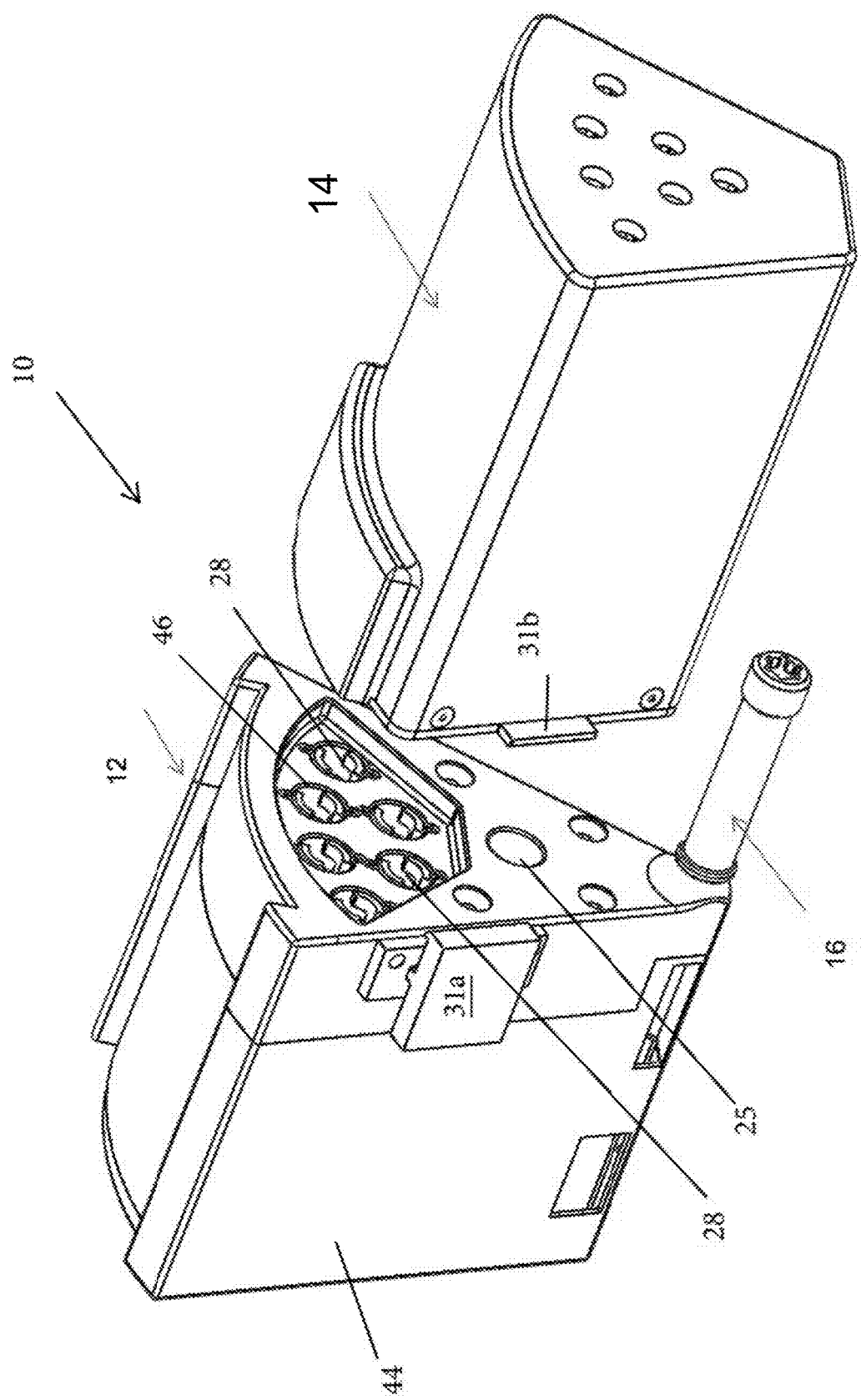
FIG. 1 is a perspective view of a first embodiment of a surgical device and motor drive assembly, showing the surgical device and motor drive separated from one another.

Referring to FIG. 1, an exemplary assembly 10 includes a surgical device 12 and a motor drive 14. The surgical device 12 is designed to be inserted through an incision (either directly or through a trocar or overtube) and positioned within a patient's body for use in performing surgery. It may be a surgical instrument having end effectors (as will be described in connection with FIG. 20), or it may be a steerable lumen device adapted to removably receive such surgical instruments. In some cases, there is a first surgical device in the form of a steerable lumen device driven using the disclosed principles, as well as a second surgical device in the form of a surgical instrument that is insertable through the lumen and that may also be steered, articulated, and/or actuated (e.g. jaw opening and closing) using the disclosed principles.

The surgical device includes actuation elements that, when pushed and/or pulled, cause active bending and/or articulation at the distal portion of the surgical device within the patient's body. The actuation elements extend through the shaft and are positioned to cause active bending/straightening of corresponding actively bendable sections, or articulation at joints or pivots, as the tension on the actuation elements is varied. The actuation elements are elongate elements (e.g. wires, rods, cables, threads, filaments etc) having distal portions anchored to the shaft and proximal portions coupled to actuation mechanisms that vary the forces (tension or compression) on the actuation elements or the positions of the actuation elements. The actuation elements generally extend between proximal and distal directions.

Figure 3B:
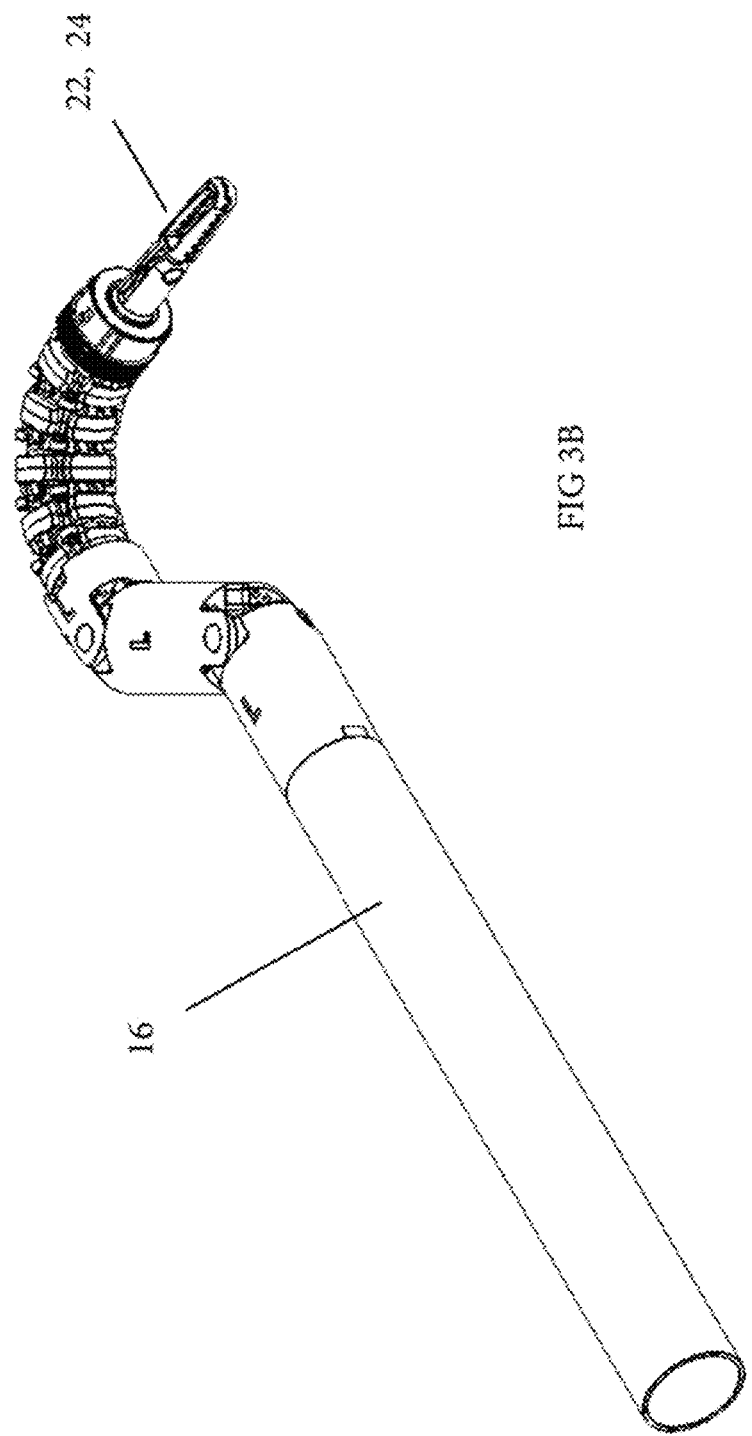
FIG. 3B is similar to FIG. 3A, but shows the end effector of a surgical instrument extending from the lumen device.

In the FIG. 1 embodiment, the surgical device 12 is illustrated as a lumen device, which includes an elongate shaft 16 having a lumen extending longitudinally through it (only the proximal portion of which is shown in FIG. 1). FIG. 3A shows one example of a distal portion of a shaft 16 and illustrates that the lumen extends to the distal end of the shaft. In use, a surgical instrument 22 (FIG. 2) is removably inserted into the proximal end of the lumen (as described below) and advanced so that its distal end effector 23 extends out the distal end of the shaft as shown in FIG. 3B. This step (assembly of the instrument 22 and surgical device 12) may be performed prior to or after insertion of the shaft 16 into the body cavity.

Referring again to FIG. 3A, the surgical device preferably has a rigid proximal portion. Towards its distal end there is one or more actively bendable or "steerable" section 18 that bends in response to movement of its elements, and/or a deployment section that will position the steerable section 18 laterally away from the longitudinal axis of the elongate shaft 16. The deployment section is useful during positioning of the surgical devices within the body cavity to allow for triangulation of multiple instruments towards a common operative site. It should be understood that the term "deployment" is not intended to convey that this section may only be used during deployment of the surgical device within the body. The deployment section may be comprised of one or more joints 20 that articulates in response to movement of corresponding actuation elements. The FIG. 3A embodiment includes both a steerable section 18 that can be steered in two degrees of freedom using steering actuation elements (e.g. three or four such elements) terminating at the distal end of the steerable section, and articulating joints 20 (as the deployment section) that are pivoted using one or two articulation actuation elements to move the distal end of the shaft laterally outward or inward in one degree of freedom. In alternative embodiments, the deployment section may be actively bendable rather than articulating. (See e.g. FIG. 18) The numbers and combinations of actively bendable and jointed articulating sections, degrees of freedom, and actuation elements can be varied from what is shown herein without deviating from the scope of the present invention. Various designs for steerable and articulating sections of instruments are known in the prior art, and so the particular details of those sections will not be discussed here.

The motor drive 14 (FIG. 1) houses the motors whose output is used to drive the actuation elements for the steerable and/or articulating sections, as applicable. The motor drive 14 is preferably supported within the surgical procedure room using a support arm or alternate support. Multiple such support arms may be used to support multiple motor drives, allowing multiple ones of the system 10 to be used in a surgical procedure, with the surgical device shafts 16 extending through a common incision or separate incisions. In other embodiments, the system will include two or more such motor drives 14, each having an associated surgical device 12. In such cases, a common support arm might support two or more motor drives so that two or more driven surgical devices 12 may extend into a patient through a common incision or through multiple incisions. In some cases, one of the surgical devices 12 might be a scope used to observe the procedure.

Figure 4A:
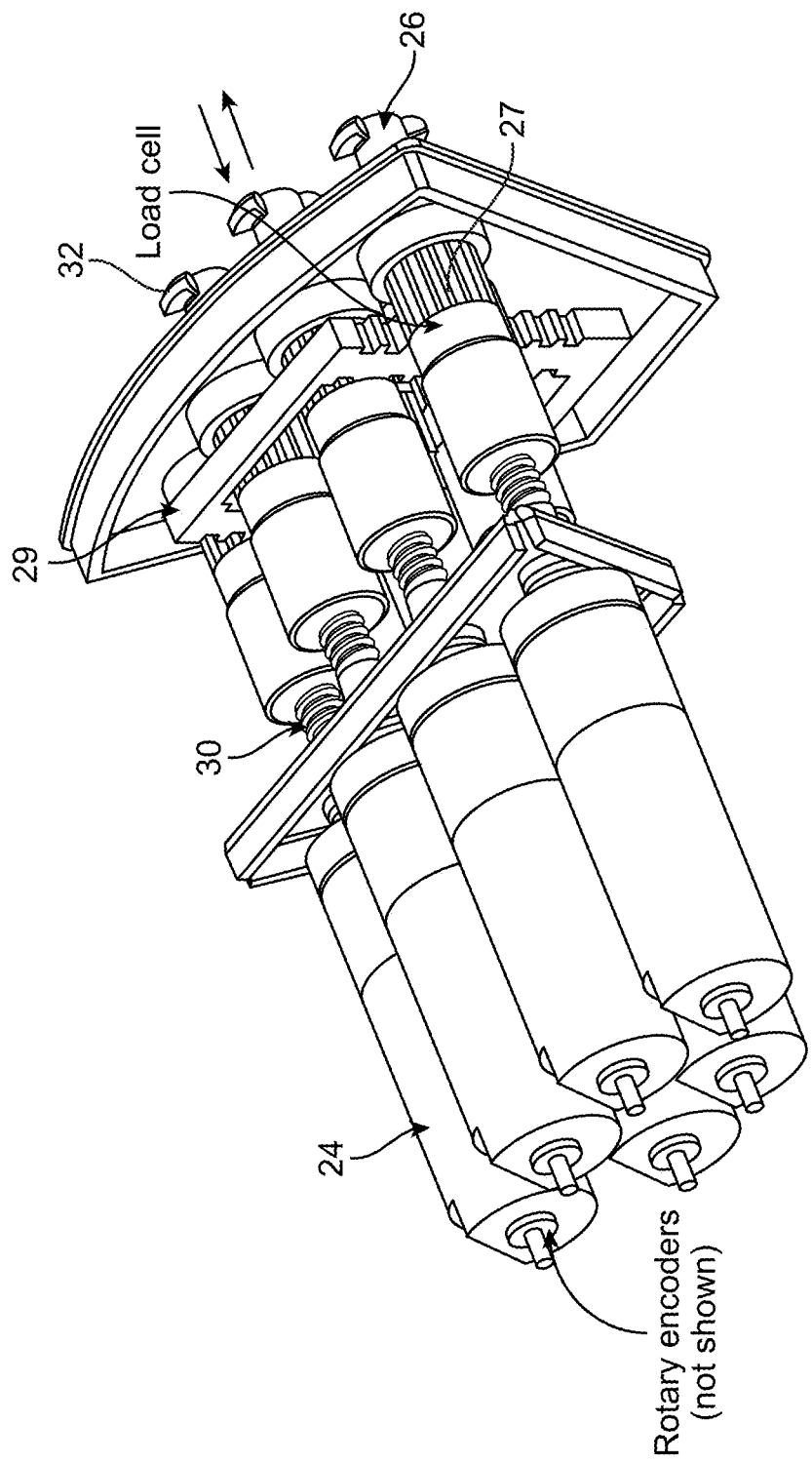
FIG. 4A is a perspective view of the motor drive with the housing removed.

FIG. 4A(i) shows the motor drive 14 with its housing removed. The motor drive 14 includes motors 24 and output elements 26. In FIG. 1, the output elements of the motor drive 14 are not visible, but it can be appreciated that when the motor drive 14 and surgical device 12 are assembled, each such output element 26 is coupled to or engaged with a corresponding input element 28 of the surgical device 12, or otherwise positioned to cause each input element 28 to move in accordance with its corresponding output element 26.

Referring again to FIG. 4A(i), in general, the motor drive 14 is configured to transfer linear motion from motors 24 to output elements 26. In this embodiment lead screw drives 30 are used for this purpose. Thus, when a motor 24 is energized, its corresponding output element 26 translates linearly towards the motor to thus pull the associated input element 28 of the surgical device (FIG. 1), and/or its corresponding output element 26 translates linearly away from the motor to thus push the associated input element 28 of the surgical device.

In the illustrated embodiments, each input element and its corresponding output element translates along a common axis. The interface between the output elements 26 and the input elements 28 places the output elements 26 and input elements 28 in a drive relationship, i.e. a relationship where linear translation of the output elements 26 directly causes linear translation of the input elements 28. This interface can take a variety of forms, each of which can be achieved without penetrating the material of the drape extending between the motor drive 14 and the surgical device 12 (even though the drape is positioned between the output elements 26 and input elements 28).

As an example, a bayonet connection can be used, in which the output elements 26 have radial elements such as tabs 32 (FIG. 4A(i)) or pins, and in which the input elements 28 have slots 34 (FIG. 5B). The slots 34 receive the radial elements 32 when the surgical device 12 and motor drive 14 are brought together (shown schematically by an arrow in FIG. 4B(ii)). Capture elements 36 (FIG. 5B) of the input elements 28 capture the tabs 32 within the second slots 35 when the output elements 26 are axially rotated a small amount (e.g. ¼ turn) relative to the input elements 28 after the tabs are inserted into slots 34, as indicated schematically by the curved arrow in FIG. 4B(iii). This method of engagement is similar to the way in which a camera lens is secured to a camera. The male and female components can be reversed in this configuration.

Referring again to FIG. 4A(i), the output elements 26 may be coupled to gears 27 disposed in motor drive housing. A gear rack 29 positioned within the housing has teeth engaged within each of the gears 27. When the tabs 32 of the output elements 26 are placed into the slots 34 of the input elements 28 during mounting of the surgical device 12 to the motor drive 14, the gear rack 29 may be moved linearly to simultaneously turn the gears 27, resulting in the simultaneous rotation of the output elements 26 to capture the tabs 32 within the capture elements 36 of the input elements 28.

Various alternative configurations for releasably connecting the output and input elements 26, 28 might instead be used. See, for example, the clip-type connection shown in FIG. 4C(i), in which the surgical device 12 is initially advanced to the motor drive 14 (FIG. 4C(iii)) and then rotated to allow the input elements 28 (not shown) to swing into engagement with lateral openings in the output elements 26 when the surgical device is rotated as indicated by the arrow in FIG. 4C(ii).

Other alternative arrangements for connecting the output and input elements include other mechanical connections as well as magnetic interfaces. Magnetic interfaces may be ones where the drape material is clamped or sandwiched between an output element 26 and an input element 24 that are magnetically connected (i.e. but for the presence of the drape, the output and input elements 26, 28 would be touching). In other embodiments, the magnetic interfaces may be ones where there is a gap between the output element 26 and input element 24. In such embodiments, the drape extends between the output and input elements but is not clamped or sandwiched between them.

Figure 19:
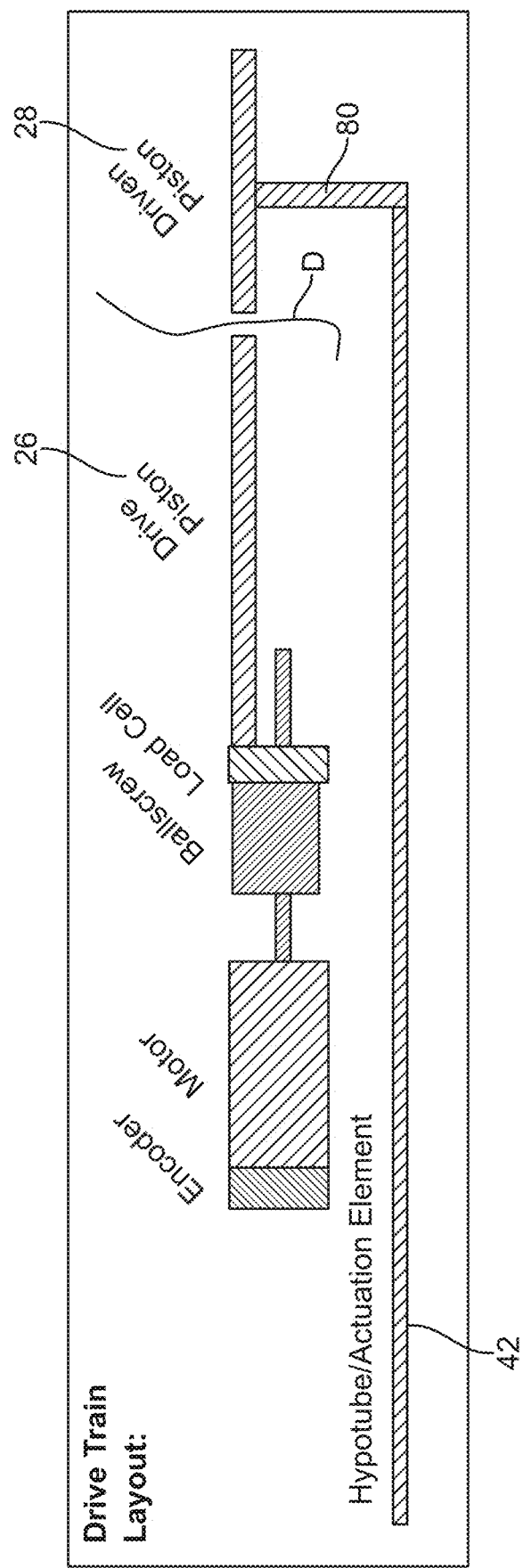
FIG. 19 schematically illustrates a drive train assembly, including an alternative surgical device subsystem.

In some embodiments, the input elements 28 and output elements 26 are not connected to one another, but simply push against one another (with the drape D remaining between them, as illustrated schematically in FIG. 19). For example, the input and output elements might be so closely spaced that but for the drape they would be touching, or there might be a very small gap between them (with the drape disposed within that gap), The system may have features that aid the user in docking the surgical device 12 and motor drive 14. For example, referring to FIG. 1, either of these components might include a guide hole 25 for receiving a guide pin (not shown) on the other component. Latch features 31a, 31b might also be included on the housings of the components so as to maintain the components in their docked arrangement.

The surgical device 12 includes a subsystem 38 that transfers the linear motion received from the output elements 26 of the motor drive 14 to the actuation elements used for steering and/or articulation of the shaft of the surgical device 12. The linear motion received from the output elements 26 can be transferred to the actuation elements 42 using pivotal, linear, or rotary means (including rotary means employing pulleys).

Referring to the exploded view of FIG. 2, subsystem 38 of the illustrated embodiment includes the input elements 28, linkage systems 40, and actuation elements 42. The subsystem 38 is enclosed within a housing 44, with the input elements 28 exposed through openings 46 in the housing for engagement with the output elements 26 of the motor drive 14 (not shown in FIG. 2, but see FIG. 1).

Figure 6B:
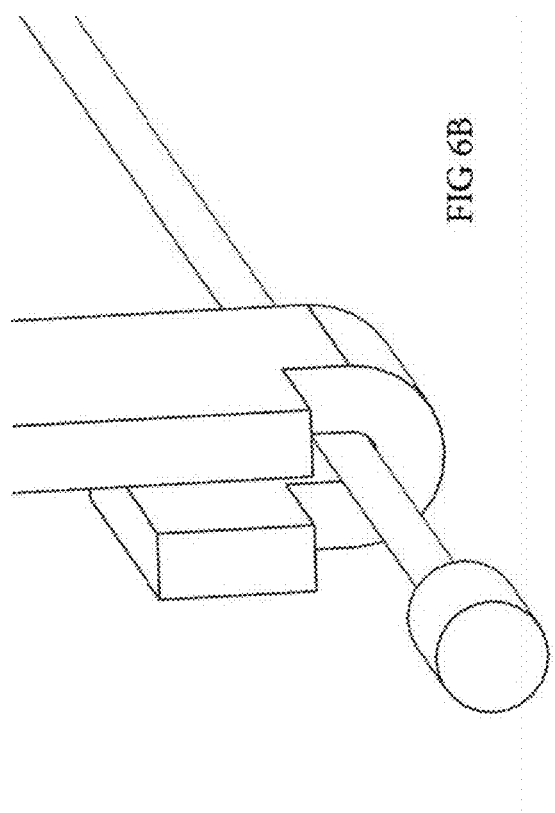
FIGS. 6A and 6B are perspective views showing the attachment of an actuation cable to an arm of a linkage assembly.
Figure 6A:
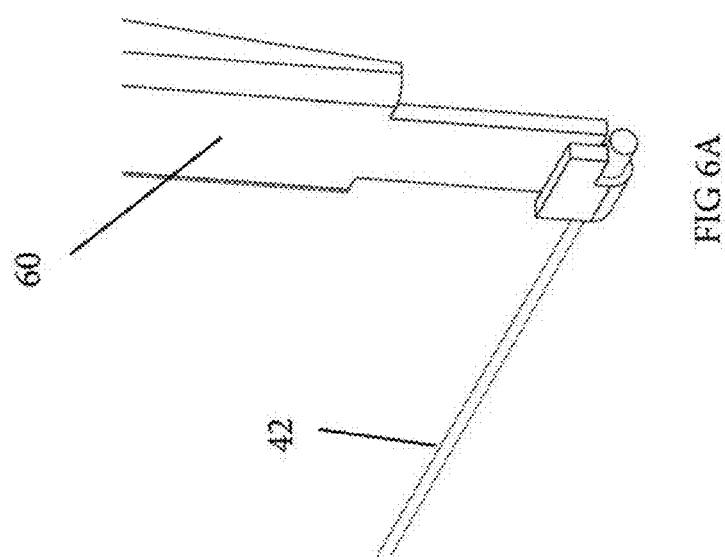

One example of a linkage system 40 is shown in FIGS. 5A and 5B and includes a first arm 48 on which the input element 28 is positioned. A second arm 50 has a first end pivotally attached to the first arm 48, and a second end that serves as an attachment point 52 for an actuation element 42 (element 42 not shown in FIGS. 5A-5B but see FIGS. 6A-6B) The actuation element 42 may be engaged to the second arm 50 including various techniques, including crimping, welding, cable wrap, etc.

Each linkage system 40 converts the linear motion its input element 28 receives from the corresponding output element 26 of the motor drive into pivotal motion, which is then used to pull the corresponding actuation element 42. As best shown in FIGS. 7A and 7B, each of the second arms 50 is mounted within the surgical device's housing such that it can pivot relative to the housing about an intermediate pivot 54. With this arrangement, when the input element 28 is moved in a first direction as indicated by arrow A in FIG. 7B (which in this embodiment is the result of pulling on the input element 28 by the corresponding output element 26, not shown, of the motor drive), the second arm 50 pivots about the intermediate pivot 54. This causes the attachment point 52 for the actuation cable to move in an opposite direction as indicated by arrow B (which, in this embodiment, results in a pulling of the actuation element 42, not shown, that is attached to the attachment point 52). It should be understood that the linkage arrangement is shown by way of example, as other mechanical structures or linkage arrangements for transferring the linear movement of the output element 26 to a mechanism for pulling or pushing the corresponding actuation element might instead be used. As but one additional example, FIGS. 10A and 10B show an alternative second arm 50a that may be used in the linkage systems 40 so that pushing on the input element 28 (not shown but see FIGS. 7A and 7B) results in pulling of the actuation elements 42. In this embodiment, each second arm 50a includes a first section 60a on which the input element 28 is mounted and a second section 60b carrying the attachment point 52 for the cable element. Each section is mounted to the surrounding housing at a pivot 54a, 54b. The sections 60a, 60b are in contact with one another such that pushing against the output element (not shown) as indicated by arrow C causes pivotal rotation of section 60a about pivot 54a in a first direction, which in turn pushes section 60b about pivot 54b. This causes the attachment point 52 to pull the cable as indicated by arrow D. Conversely, pivotal rotation of section 60b about pivot 54b in a second direction (opposite to the first direction) will cause section 60a to pivot about pivot 54a.

A draping system for use in covering the motor device 14 might include features that accommodate the (push or pull) movement at the interface between the output elements 26 and input elements 28 without tearing the drape. Such features might include a plurality of pre-formed bellows or pockets, each positioned over one of the output elements 26, or they might include regions of material that are more elastic than the surrounding drape material. Alternatively, the drape can be provided without any such features if the elasticity of the drape is sufficient for relative movement of the output elements without perforating the drape. Alternative drape designs might include mechanical features attached to the drape to assist in the coupling of motion between output elements 26 and the input elements 28.

Each input element 28 (and thus each motor and corresponding output element) is operatively associated with a different one of the actuation elements 42. As discussed, the illustrated embodiment uses six actuation elements 42 (e.g. 4 for movement of the actively bendable section in 2 degrees of freedom and 2 for movement of the deployment section in 1 degree of freedom). Six drive linkages are therefor used for moving those actuation elements 42. Other embodiments might use as few as one actuation elements 42, while some might use more than six. FIG. 8 illustrates a cable interface for the six-element surgical device 12 shown in FIG. 1. It shows the second arms 50 of each linkage, as well as the associated actuation cables 42. The actuation cables 42 run along the outer surface of an inner tubular shaft 56 and feed into the shaft 16 (not shown in FIG. 8, but see FIGS. 3A and 3B). One or more cable guides 58a, b retain the cables 42 against the surface of the inner shaft 56. See also FIG. 9. Note that in this arrangement, the linkages are arranged to place four of the cable attachment points 52 in a more proximal position relative to the other two cable attachment points 52. Other arrangements can be used as alternatives, include those in which all cable attachment points 52 are spaced from the distal end of the surgical device's shaft by the same longitudinal distance. Cables can also be placed circumferentially in a non-symmetrical pattern.

The housings for the surgical device and motor drive may be shaped in numerous different ways, and the components within those housing may be arranged in a variety of configurations. FIG. 11 shows an alternative housing shape for the surgical device 12 as well as an alternative arrangement for the input elements 28.

As discussed above, this particular embodiment is one in which the surgical device 12 is a lumen device, and in which a surgical instrument 22 is passed through the lumen of the lumen device. Referring to FIG. 2, the instrument 22 includes an elongate shaft with a distal end effector. The shaft may include a rigid proximal section, and a passively flexible distal section. When the system is assembled, the flexible distal section of the instrument shaft is disposed within the controllably moveable distal part 18 (where articulation and/or steering occurs) of the shaft 16 of the lumen device.

At the proximal end of the instrument 22 is an instrument pack 62 that may include one or more motors and associated electronics controlled by the user interface to actuate the end effector of the instrument 22 by engaging actuation elements operatively associated with the end effectors in a manner known in the art. One or more motors might also be positioned to drive movement of a distal part of the shaft in one or more additional degrees of freedom, through bending or articulation. In such embodiments, the instrument shaft might have features similar to those shown on the shafts of FIG. 3A or 18, or other features of articulated or jointed shafts known in the art.

If the instrument is a manually actuated instrument, the instrument pack may be replaced by a handle that can be operated by the hand of a user to effect (e.g. for opening and closing of a jaw on the instrument shaft).

As shown in FIG. 2, the instrument 22 is inserted into a port 64 on a proximal part of the surgical device 12 and advanced to extend the instrument shaft through the shaft 16 of the surgical device until the end effector extends from the distal end of the shaft 16 as shown in FIG. 3A. As shown in FIGS. 12A-12B, the instrument pack 62 may include a longitudinally extending portion 66 having electrical contacts (not visible) that make electrical contact with contacts 68 on the housing of the motor drive 14. Note that in FIGS. 12A-12B, the surgical device 12 is not shown. In use, its housing would be disposed between the instrument pack 22 and the motor drive 14, and its shaft 16 would extend adjacent to the motor drive 14 as shown in FIG. 1. The electrical contacts of the instrument pack and motor drive can communicate electrical power to the instrument pack for energizing its motors, and can further communicate information between the motor drive 14 and the instrument pack 62. Information communicated might include usage information relating to the number of times or minutes the instrument has been used (to prevent use of the instrument beyond its recommended usage limit), information concerning the type of tool so that the system can select scaling factors most suitable for the instrument, or other information, or other information. Electrical contacts may be built into the drape to facilitate electrical coupling between the contacts of the instrument pack and those of the motor drive housing.

It should be noted that information might be communicated using other means, such as RFID or optical communication means. The instrument pack 62 and motor drive 14 might further include mechanical features 70 that allow them to releasably latch together.

Referring again to FIG. 4A, the control system used to control steering/articulation of the surgical device may receive feedback from load cells associated with each (or a plurality) of the output shafts 26 or drive pistons so as to generate signals representing the force applied to the output shafts 26 (or drive pistons), rotary encoders that determine the rotational positions of the motors, and/or other sensors positioned to detect linear displacement of components of the drive assembly. These are also schematically depicted in FIG. 19. Signals from such sensors may be used, alone or in combination, by the control system to control steering/articulation and to thus optimize steering/articulation accuracy.

Additional sensors may be positioned to sense the gap formed between output and input shafts 26, 28 or pistons, so as to detect whether the gap between corresponding input and output pistons is approaching a point where an input piston might become too far out of the range of the output piston to be controlled by the output piston.

FIGS. 13-16 show features of a surgical system that includes two modified steerable lumen assemblies, each being a modified version of the steerable lumen surgical device (12, 38a, 44, 16, 18) described in connection with the FIG. 1 embodiment. A passively flexible surgical instrument 22 extends through the lumen of the surgical device. A motor drive (not shown) is housed within a base 72 that is slidable relative to a housing. The motor drive is controlled by the control system to effect bending and deployment of the shaft of the surgical device (which in this embodiment is the lumen device). The motor drive has output/drive elements that are operatively associated with input elements of the surgical device 12 using features of the type described with the first embodiment. The motor drive's output elements translate linearly to transfer motion to the linearly moveable input elements. A drape may extend between input elements and output elements as described with respect to the first embodiment. In one embodiment, there are six motors, four that cause steering of the lumen's steerable section (e.g. with each motor driving one of four actuation elements) and two that move the deployment section 21 (FIGS. 17 and 18) by driving two additional actuation elements. As described above, the steerable section and deployment section may have a variety of configurations known in the art.

The instrument 22 has an instrument motor pack 62 that can cause jaw actuation and/or axial rolling of the surgical instrument relative to the lumen device in a manner similar to the assembly of the first embodiment, and that can also couple electrical energy to the end effector of the instrument and optionally control one or more additional degree of freedom of motion (e.g. articulation or bending of the shaft supporting the end effector). The instrument pack 62 could be configured as one or more "stackable" units, each providing one or more of those functions. The surgical device 12 can also allow for mechanical transfer of work through the housing to the instrument pack.

The base 72 is disposed on a housing 74 and is slidable over the housing in distal/proximal directions. Motors in the housing are activated by the system to linearly translate the base. This moves the steerable lumen device (and the instrument passing through it) in the distal to proximal "Z" direction, to advance/withdraw the tip of the surgical device (and the instrument) within the patient.

Figure 13:
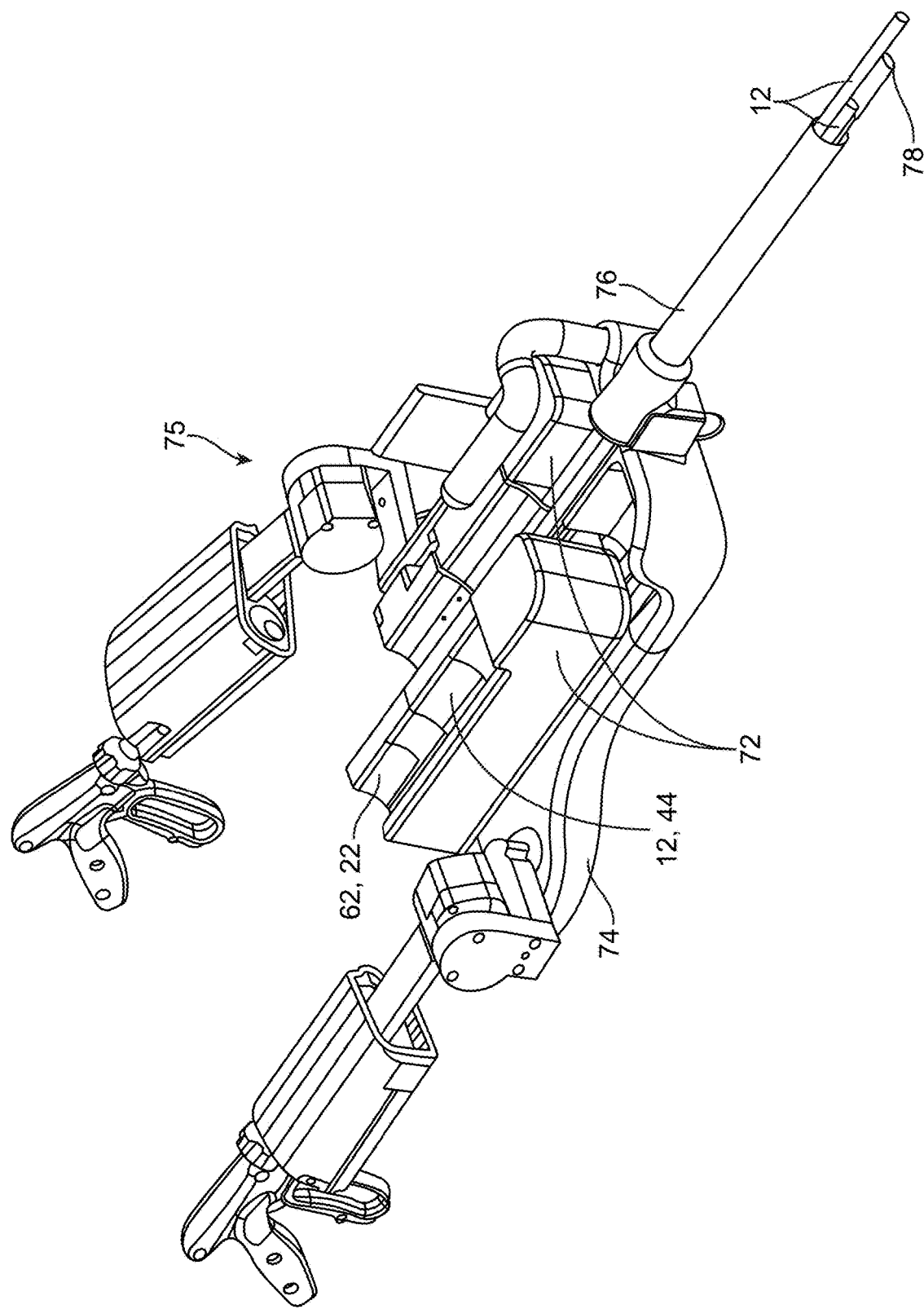
FIGS. 13 through 16 illustrate a second embodiment of a surgical system, which includes modified versions of steerable lumen/surgical device and motor drive assemblies.
Figure 14:
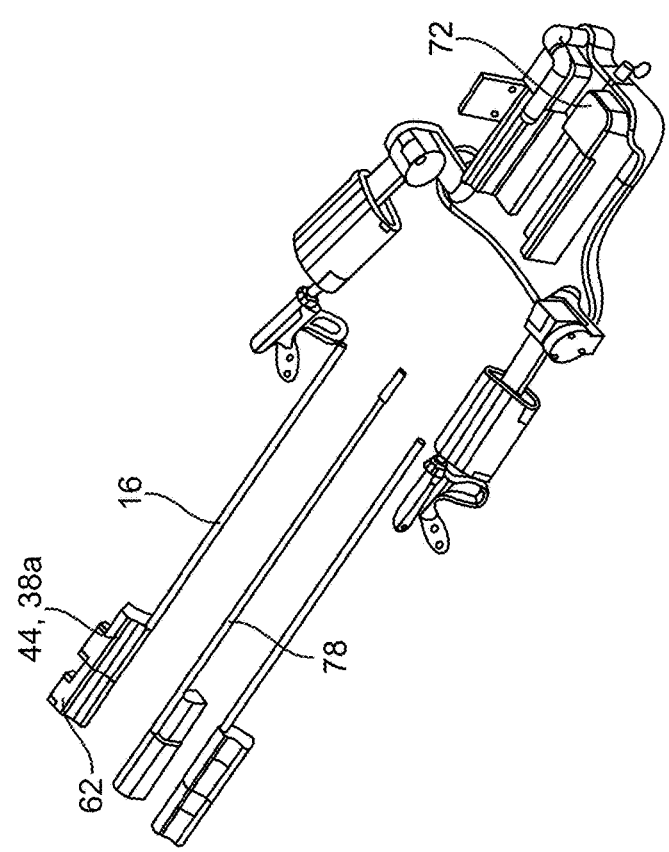
Figure 16:
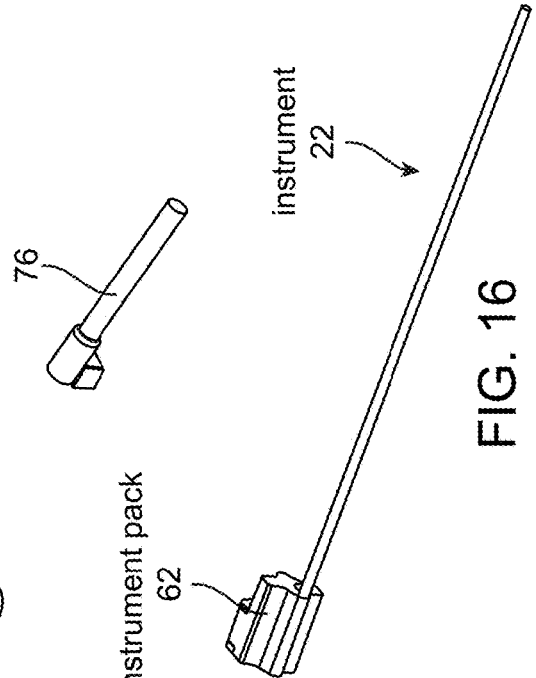
Figure 15:
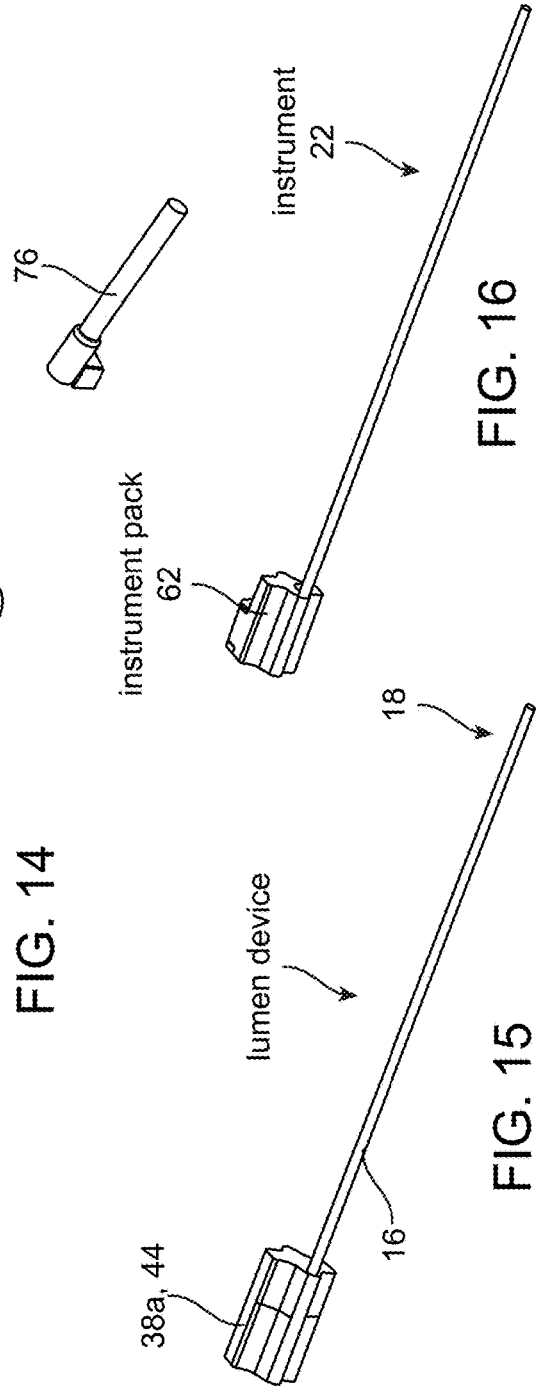

Multiple bases 72 may be arranged on the housing 74. In the present embodiment, two bases are on the housing 74. Each base is configured to receive a corresponding lumen device and surgical instrument. The distal ends of the lumen devices extend into an insertion tube 76 positionable through an incision to place the distal ends of the lumen devices and instruments within the body cavity. A scope used to visualize the procedure within the body cavity may also extend through the insertion tube 76. The head of such a scope 78 is shown in FIG. 13.

Input devices 75 allow a surgeon to provide input to the system for the purpose of driving the motors to move the surgical device and the instrument. The input devices 75 may optionally have handles shaped like laparoscopic devices. The handles are mounted on an input encoder arrangement similar to that shown and described in US Publication No. 2014/0107665, which is incorporated herein by reference.

Figure 17:
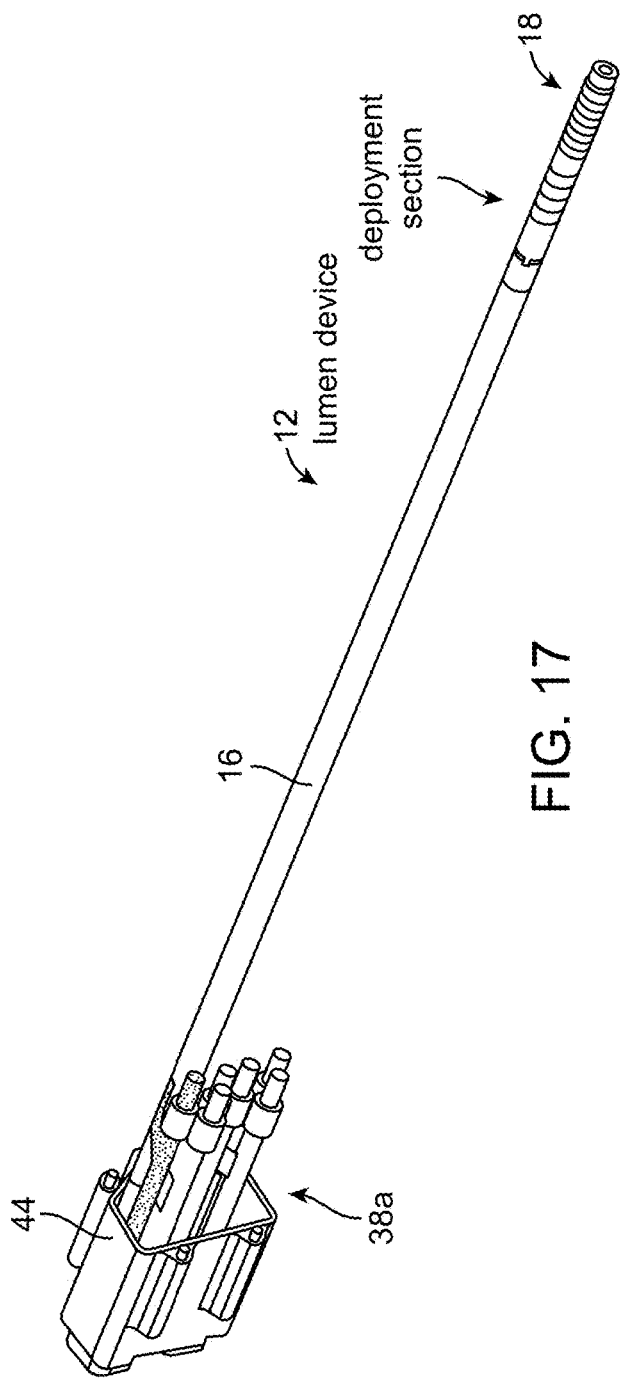
FIGS. 17 and 18 illustrate an alternate embodiment of a surgical device which may be used in the assemblies of the first and second embodiments.
Figure 18:
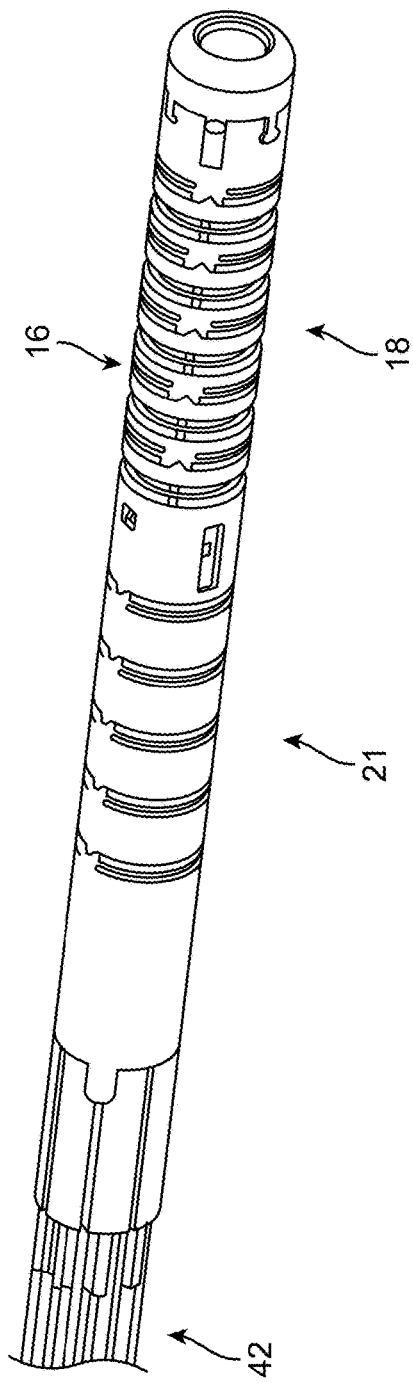

FIGS. 17-19 illustrate an alternative surgical device for use with systems of the type described above. The surgical device uses a simplified subsystem 38a for transferring motion from the input elements 28a to the actuation elements 42. As can be seen in the schematic of FIG. 19, each input element is connected by a rigid link 80 to a corresponding actuation element that extends within the shaft of the surgical device to an anchor point. In this embodiment, the actuation element comprises hypotube, although other types of element can be used. The hypotube extends along the shafts length to its anchor point within the surgical device shaft 16, or only a proximal portion of the actuation element may be made of hypotube with a distal portion being made of cable, wire, filament, etc. In this embodiment, activation of the motor advances output element 26, which pushes input element 28a on the other side of the drape D.

Figure 20:
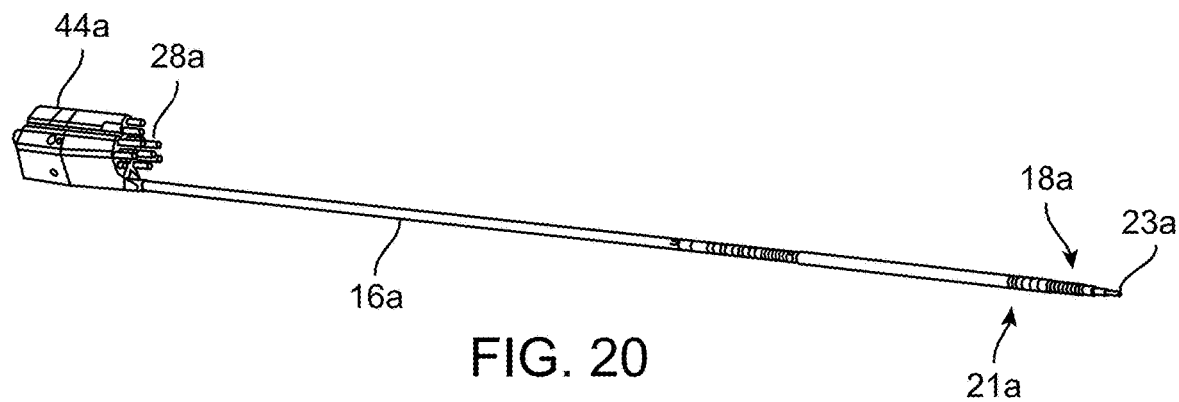
FIG. 20 is a perspective view of a surgical device which may be used in the assemblies of the first and second embodiments.
Figure 21:
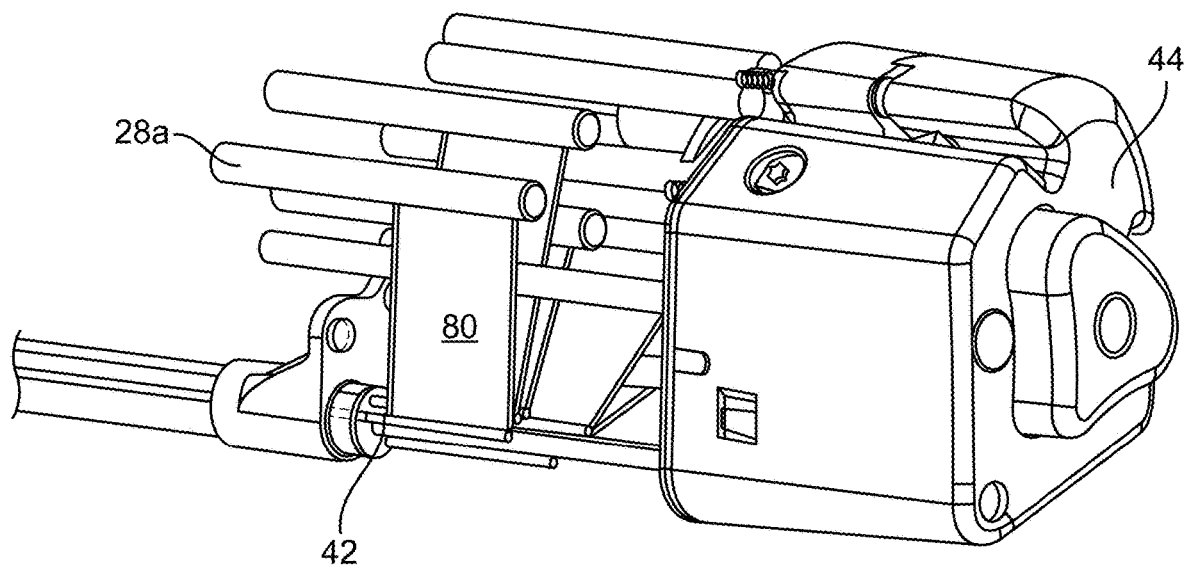
FIG. 21 shows the proximal portion of the surgical device of FIG. 20, with a portion of the housing removed to allow the subsystem to be viewed.
Figure 22:
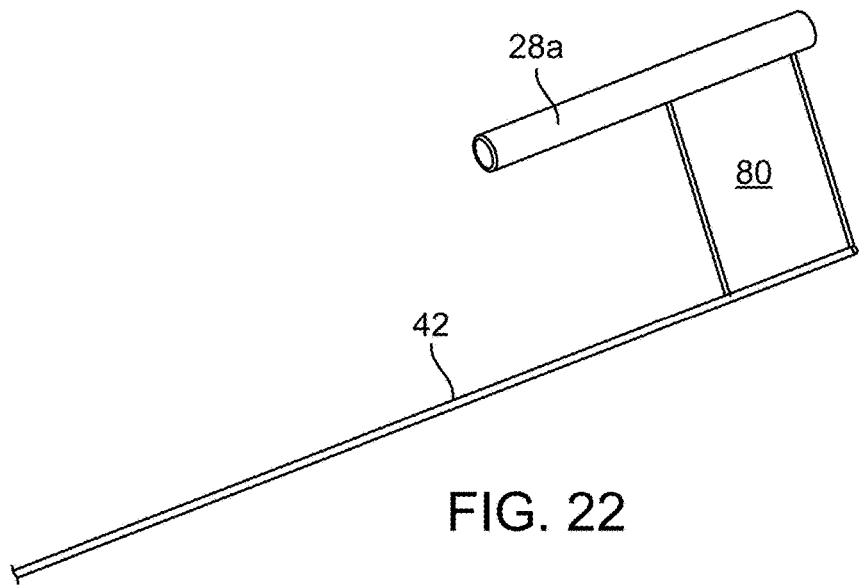
FIG. 22 schematically shows features of the subsystem shown in FIG. 21.

The surgical device of FIG. 18 also differs from that of the first embodiment in that it includes two actively bendable sections for articulation and deployment. The articulation section is preferably bendable in two degrees of freedom, and the deployment section is bendable in one or two degrees of freedom. As can be seen in FIG. 20, a shaft might include an additional bending section that is more proximal than the others, to provide additional degrees of freedom.

As discussed above, the surgical device 12 might be a surgical instrument with an end effector, rather than a lumen device that receives a surgical instrument through it. In such an embodiment, an end effector, scope, etc. would be positioned on the shaft 16. The detachable motor drive 14 would be used to control movement of the instrument or scope, such as articulation or bending, deployment, jaw actuation, axial rotation of the instrument shaft or of the end effector relative to the shaft, in each case by transferring linear motion from the motor drive's output shafts to the instruments instrument shafts and causing actuation components in the instrument 16 to be driven in response to movement of the motor drive's output shafts. An instrument of this type might be mounted to a support such as a positioning arm as is discussed above (either individually or in combination with other surgical instruments and drive units, including a cluster of instruments extending through a common insertion tube), or it might be a handle-held instrument.

Figure 23:
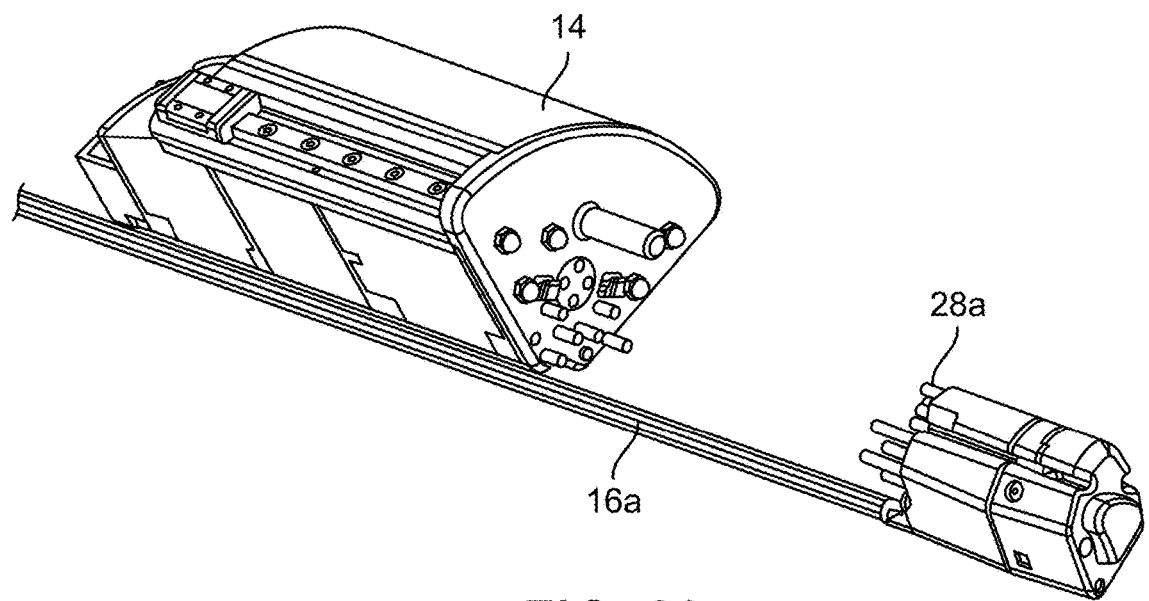
FIG. 23 shows a motor drive and a proximal portion of the instrument of FIG. 20. The drape that extends between the output elements of the motor drive and the input elements of the surgical device is not shown.

FIGS. 20-24 illustrate components of a surgical system assembly that is similar to the assembly of FIG. 1, but in which the surgical device 12b is a surgical instrument having an end effector 23a. This embodiment uses the subsystem illustrated in FIG. 19 to transfer motion from the input elements 28a to the actuation elements 42 within the surgical device 12a. As shown in FIG. 23, output elements 26a extend from the housing of the motor drive 14, and the input elements 28a extend from the housing of the surgical device 12a.

Figure 24:
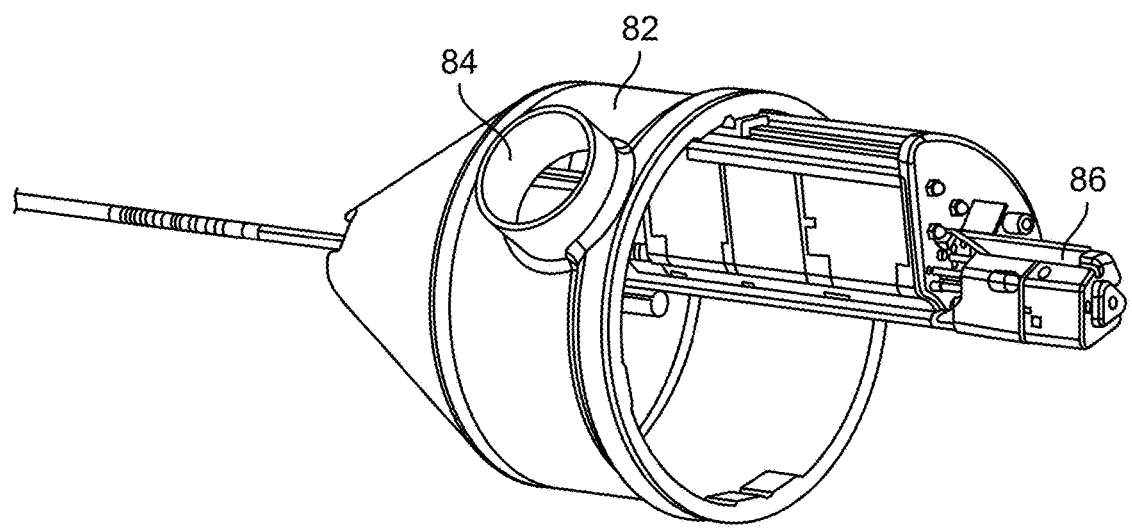
FIG. 24 shows the motor drive and instrument of FIG. 23 positioned with the input and output elements in the driving relationship.

When the motor drive 14 and surgical instrument are placed in the drive relationship shown in FIG. 24, the input and output elements are positioned on opposite sides of the drape as shown in FIG. 19. When a motor is energized to advance an output element axially towards its corresponding input element, it pushes the input element towards the surgical device housing, causing the actuation element that is coupled to that input element to be pulled.

By way of example, consider a surgical device where the actuation elements responsible for active bending of the shaft are anchored at four locations spaced 90 degrees apart. To bend the shaft in an upward direction, a first motor might be energized to cause a corresponding first input element 28a to be pushed, resulting in the pulling of the associated first actuation element and causing the shaft to bend upwardly. To then bend the shaft downwardly, a second motor is energized to cause another, second, input element 28a to be pushed, resulting in the pulling of a second actuation element anchored 180 degrees from the first actuation element, causing the shaft to bend downwardly. As the shaft moves between the upward and downward configurations, the first input element 28a moves outwardly as a result of the change in shape of the shaft 16a, and the first motor is simultaneously energized to retract the first output element 26a a corresponding amount.

Other configurations using, for example, three actuation elements for active bending of the shaft will push the appropriate combinations of input elements 28a to achieve the desired movement.

Note that while this application shows two exemplary subsystems that may be used to perform this function, alternative subsystems can be used without deviating from the scope of the invention.

The motor drive is mounted, or mountable, to a support such as a support arm of the type used for surgical systems. Mounting may be direct or via an intermediate structure. The surgical device is mounted to the support, either directly or by way of a connection to the motor drive housing or to another structure between the surgical device and the support, so that the relative positions of the motor drive housing and the surgical device (e.g. the rigid proximal portion of the shaft 16, or the housing 44) remain fixed during the surgical procedure. This maintains the input and output shafts in the drive relationship through the procedure.

In FIG. 24, the motor drive 14 is shown mounted to a housing 82 that may be used to support a plurality (up to four) such motor drive and surgical device assemblies in positions that allow the shafts of the surgical devices to extend in parallel to one another through a common incision in a body cavity. One of the surgical devices in such an arrangement may be surgical scope that can be deployed and actively bent within the body cavity using the features described herein. A mount 84 on the housing allows the housing to be connected to a support arm. Support arms that may be used for this purpose are known in the art. One such arm is illustrated in US Publication No. 2014/0107665. Features on the housing 82, motor drive housing, and/or surgical device may be used to support the motor drive and surgical device in the drive relationship. For example, support member 86 may be mounted to the motor drive 14 before or after draping, and the housing 44 of the surgical device 12 may be mounted to that support member.

The motor drives and surgical instruments described herein are components of a surgical system that includes a user input device used by a surgeon to input instructions to the surgeon as to the desired movement or actuation of the surgical devices. The surgical system further includes a control system including one or more processors that receive signals from the user input devices and from sensors of the system, and that generate commands used to drive the motors to cause active bending, deployment, actuation, etc. of the surgical devices in accordance with the user's input. A display for displaying an image obtained from a scope within the body cavity (e.g. a scope positioned and manipulated as described herein) is typically positioned in proximity to the user input device, allowing the surgeon to view the image of the procedure while s/he operates the user input device. User input devices and control systems for robotic surgical systems, and laparoscopic/endoscopic image displays are known to those skilled in the art and so details of such systems are not provided herein.

To use the system, the hospital staff positions sterile drapes over the motor drive units, with the sterile drape material extending over the output elements. This step may be performed with the motor drives mounted to the support. Surgical devices are mounted to the system to position the input elements in a drive relationship with their corresponding output shafts, with the sterile drape disposed between the input elements and output elements. During use of the system, the surgeon operates the input devices while observing the procedure on the display. The control system operates the motors in response to user input so as to articulate and actuate the surgical instruments in accordance with the user instructions.

In any of the disclosed embodiments, the motors used for driving may be replaced with other types of drivers including, without limitation, hydraulic or pneumatic drivers. Mechanical communication is possible by means of hydraulic actuation transmitted across the drape, without penetrating the drape.

While certain embodiments have been described above, it should be understood that these embodiments are presented by way of example, and not limitation. It will be apparent to persons skilled in the relevant art that various changes in form and detail may be made therein without departing from the spirit and scope of the invention. This is especially true in light of technology and terms within the relevant art(s) that may be later developed. Moreover, features of the various disclosed embodiments may be combined in various ways to produce various additional embodiments.

Any and all patents, patent applications and printed publications referred to above, including for purposes of priority, are incorporated herein by reference.

We claim:

1. A method of operating a drive assembly of a surgical system, comprising:
   providing a drive unit comprising a plurality of output elements, each output element linearly moveable in first and second directions, the second direction opposite to the first direction, providing a surgical device including a plurality of linearly moveable input elements, each input element linearly moveable in the first and second directions;
   positioning the drive unit, and surgical device, and a sterile barrier such that a plurality of the output elements are longitudinally aligned with corresponding ones of a plurality of the input elements, and the sterile barrier extends between the output and input elements;
   operating a plurality of actuators to cause select ones of actuators to linearly translate in the first or second direction, thereby causing corresponding linear translation of the corresponding input elements in the first or second direction, each output element translating along a common axis with its corresponding input element.

2. The method according to claim 1, wherein:
   the surgical device comprises an elongate shaft having a distal articulation section, and a plurality of actuation elements extending through the shaft, each of the plurality of input elements operatively associated with a corresponding one of the actuation elements;
   causing linear translation of input elements engages the corresponding actuation elements to move the elongate shaft at the distal articulation section.

3. The method of claim 2, wherein the engagement of an actuation member causing bending of an articulation section of the elongate shaft.

4. The method of claim 2, wherein the surgical device is a surgical instrument having an end effector, and wherein the engagement of an actuation member opens or closes jaws of the end effector.

5. The method of claim 2, wherein the surgical device includes a lumen, wherein the system further includes a surgical instrument having a passively flexible portion disposed within the lumen, and wherein engagement of an actuation element results in flexing of the passively flexible portion of the surgical instrument.

6. The method of claim 1, wherein positioning includes mechanically engaging a plurality of the input elements with corresponding output elements.

7. The method of claim 1, wherein positioning includes causing a plurality of the input elements to mechanically interface with corresponding output elements.

8. The method of claim 7, wherein each input element is axially spaced apart from its corresponding output element by a gap.

9. The method of claim 1, wherein positioning lacks the step of mechanically attaching the input elements to their corresponding output elements.

10. The method of claim 1, wherein positioning includes positioning a sterile barrier between the output and input elements.

11. The method of claim 10, wherein the input and output elements do not penetrate the sterile barrier.

12. The method of claim 11, wherein the sterile barrier is a flexible linear barrier and wherein translation of the output elements causes the sterile barrier to flex in the first or second direction.

13. The method of claim 10, wherein positioning includes mechanically engaging a plurality of the input elements with corresponding output elements with the sterile barrier disposed between them.

14. The method of claim 10, wherein positioning includes causing a plurality of the input elements to mechanically interface with corresponding output elements with the sterile barrier disposed between them.

* * * * *